United States Patent
Wagner et al.

(10) Patent No.: US 8,357,689 B2
(45) Date of Patent: Jan. 22, 2013

(54) SUBSTITUTED ARYLSULFONYLAMINOMETHYLPHOSPHONIC ACID DERIVATIVES, THEIR PREPARATION AND THEIR USE IN THE TREATMENT OF TYPE I AND II DIABETES MELLITUS

(75) Inventors: Holger Wagner, Mettenberg (DE); Elke Langkopf, Warthausen (DE); Matthias Eckhardt, Biberach (DE); Ruediger Streicher, Biberach (DE); Corinna Schoelch, Mittelbiberach (DE); Annette Schuler-Metz, Ulm (DE); Alexander Pautsch, Ulm (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 33 days.

(21) Appl. No.: 12/669,978

(22) PCT Filed: Jul. 25, 2008

(86) PCT No.: PCT/EP2008/059805
§ 371 (c)(1),
(2), (4) Date: Apr. 8, 2010

(87) PCT Pub. No.: WO2009/016118
PCT Pub. Date: Feb. 5, 2009

(65) Prior Publication Data
US 2010/0210594 A1 Aug. 19, 2010

(30) Foreign Application Priority Data
Jul. 27, 2007 (DE) .................. 10 2007 035 333

(51) Int. Cl.
A61K 31/404 (2006.01)
A61K 31/416 (2006.01)
A61K 31/4184 (2006.01)
A61K 31/423 (2006.01)
A61K 31/428 (2006.01)
C07D 237/04 (2006.01)
C07D 403/04 (2006.01)

(52) U.S. Cl. .............. 514/252.06; 514/255.05; 544/239; 544/405

(58) Field of Classification Search .................. 544/239, 544/405
See application file for complete search history.

(56) References Cited

U.S. PATENT DOCUMENTS

| | | |
|---|---|---|
| 6,114,532 A | 9/2000 | Ries et al. |
| 6,710,046 B1 | 3/2004 | Matsumori |
| 6,812,250 B2 | 11/2004 | Defossa et al. |
| 7,138,414 B2 | 11/2006 | Schoenafinger et al. |
| 7,223,796 B2 | 5/2007 | Defossa et al. |
| 7,262,220 B2 | 8/2007 | Defossa et al. |
| 7,989,622 B2 | 8/2011 | Bajjalieh et al. |
| 2006/0142250 A1 | 6/2006 | Blaskovich et al. |
| 2006/0205713 A1 | 9/2006 | Gschwend et al. |
| 2010/0093703 A1 | 4/2010 | Wagner et al. |
| 2010/0130557 A1 | 5/2010 | Wagner et al. |
| 2010/0210594 A1 | 8/2010 | Wagner et al. |
| 2010/0210595 A1 | 8/2010 | Wagner et al. |
| 2011/0003759 A1 | 1/2011 | Stein et al. |
| 2011/0137032 A1 | 6/2011 | Endo et al. |
| 2011/0269737 A1 | 11/2011 | Wagner et al. |
| 2012/0059014 A1 | 3/2012 | Barba et al. |
| 2012/0071512 A1 | 3/2012 | Hu et al. |

FOREIGN PATENT DOCUMENTS

| | | |
|---|---|---|
| EP | 0604657 A1 | 7/1994 |
| EP | 0638581 A1 | 2/1995 |
| EP | 1074542 A1 | 2/2001 |
| JP | 2005206492 A | 8/2005 |
| WO | 9928297 A1 | 6/1999 |
| WO | 0170754 A1 | 9/2001 |
| WO | 02096864 A1 | 12/2002 |
| WO | 03084922 A1 | 10/2003 |
| WO | 2004007437 A1 | 1/2004 |
| WO | 2004007455 A1 | 1/2004 |
| WO | 2004104001 A2 | 12/2004 |
| WO | 2005/013976 A1 | 2/2005 |
| WO | 2005/013977 A1 | 2/2005 |
| WO | 2005/013978 A1 | 2/2005 |
| WO | 2005/024535 A2 | 3/2005 |
| WO | 2006024535 A1 | 3/2006 |
| WO | 2006034418 A2 | 3/2006 |
| WO | 2006052722 A1 | 5/2006 |
| WO | 2007044729 A2 | 4/2007 |
| WO | 2008/099000 A2 | 8/2008 |
| WO | 2008/103354 A2 | 8/2008 |

(Continued)

OTHER PUBLICATIONS

International Search Report for PCT/EP2008/059805 mailed Nov. 6, 2008.

(Continued)

*Primary Examiner* — Shawquia Young
(74) *Attorney, Agent, or Firm* — Michael P. Morris; Mary-Ellen M. Devlin; Usha R. Patel

(57) ABSTRACT

The present invention relates to substituted arylsulphony-laminomethyl-phosphonic acid derivatives of general formula

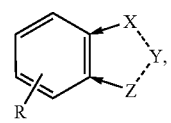

(I)

wherein R, X, Y and Z are defined as in claim 1, the tautomers, enantiomers, diastereomers, mixtures thereof and salts thereof which have valuable pharmacological properties, particularly the suppression of the interaction of glycogen phosphorylase a with the $G_L$ subunit of glycogen-associated protein phosphatase 1 (PP1), and their use as pharmaceutical compositions.

11 Claims, No Drawings

FOREIGN PATENT DOCUMENTS

| WO | 2008/113760 A2 | 9/2008 |
| WO | 2009/016118 A1 | 2/2009 |
| WO | 2009/016119 A1 | 2/2009 |
| WO | 2009030715 A1 | 3/2009 |
| WO | 2010026096 A1 | 3/2010 |

OTHER PUBLICATIONS

U.S. Appl. No. 12/530,507, filed Dec. 4, 2009.
U.S. Appl. No. 12/527,249, filed Oct. 8, 2009.
U.S. Appl. No. 12/669,978, filed Jan. 21, 2010.
U.S. Appl. No. 12/669,979, filed Jan. 21, 2010.
Abstract in English for JP200506492 cited herein.
Chen, et al. "Discovering Benzamide Derivatives as Glycogen Phosphorylase Inhibitors and Their Binding Site at the Enzyme" 15 Bioorg. & Med. Chem. pp. 6763-6774 (2007).
Cohen, Philip "The Twentieth Centry Struggle to Decipher Insulin Signalling" Nature Reviews Molecular Cell Biology, vol. 7, Nov. 2006, pp. 867-874.
International Search Report for PCT/EP2008/061651 mailed Dec. 1, 2008.
Jordan, V Craig, "Tamoxifen: A Most Unlikely Pioneering Medicine" Nature Reviews Drug Discovery, vol. 2, Mar. 2003, pp. 205-213.
Martin, Yvonne C. et al. "Do Structurally Similar Molecules Have Similar Biological Activity?" 45 J. Med. Chem. pp. 4350-4358 (2002).
Zibrova, Darya et al., "Inhibition of the interaction between protein phosphatase 1 glycogen-targeting subunit and glycogen phosphorylase increases glycogen synthesis in primary rat hepatocytes" Biochem Journal, 2008, 412, pp. 359-365.
WO2006052722 (Part 1 of 2) International Publication Date: May 18, 2006. Applicant: Smithkline Beecham Corporation, Inventors: Evans, Karen et al., Title: "Glycogen Phosphorylase Inhibitor Compounds and Pharmaceutical Compositions Thereof" Total pp. 681. This PCT publication is too large for EFS submission via the foreign patent section, therefore submitting in two parts in the NPL section. pp. 1-340.
WO2006052722 (Part 1 of 2) International Publication Date: May 18, 2006. Applicant: Smithkline Beecham Corporation, Inventors: Evans, Karen et al., Title: "Glycogen Phosphorylase Inhibitor Compounds and Pharmaceutical Compositions Thereof" Total pp. 681. This PCT publication is too large for EFS submission via the foreign patent section, therefore submitting in two parts in the NPL section. pp. 341-681.

SUBSTITUTED ARYLSULFONYLAMINOMETHYLPHOSPHONIC ACID DERIVATIVES, THEIR PREPARATION AND THEIR USE IN THE TREATMENT OF TYPE I AND II DIABETES MELLITUS

This application is the national stage filing under 35 U.S.C. §371 of International Application No. PCT/EP2008/059805, filed Jul. 25, 2008, which claims the benefit of German Patent Application No. DE102007035333.4, filed Jul. 27, 2007, each of which is incorporated by reference in its entirety.

The present invention relates to substituted arylsulphonylaminomethyl-phosphonic acid derivatives of general formula I

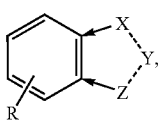

(I)

wherein the groups R, X, Y and Z are defined as hereinafter, including the tautomers, stereoisomers, mixtures thereof and salts thereof. This invention further relates to pharmaceutical compositions containing a compound of formula I according to the invention as well as the use of a compound according to the invention for preparing a pharmaceutical composition for the treatment of metabolic disorders, particularly type 1 or type 2 diabetes mellitus. The invention also relates to processes for preparing a pharmaceutical composition as well as a compound according to the invention.

Compounds of formula I are suitable for preventing the inhibiting effect of glycogen phosphorylase on the activity of glycogen synthase by stopping the interaction of glycogen phosphorylase a with the $G_L$ subunit of glycogen-associated protein phosphatase 1 (PP1). Compounds with these properties stimulate glycogen synthesis and are proposed for the treatment of metabolic disorders, particularly diabetes (P. Cohen, *Nature Reviews Molecular Cell Biology* 2006, 7, 867-874).

AIM OF THE INVENTION

The aim of the present invention is to provide new arylsulphonylamino-methylphosphonic acid derivatives that suppress the interaction of glycogen phosphorylase a with the $G_L$ subunit of glycogen-associated protein phosphatase 1 (PP1).

A further aim of the present invention is to provide new pharmaceutical compositions that are suitable for the prevention and/or treatment of metabolic disorders, particularly diabetes.

Another aim of this invention is to provide a process for preparing the compounds according to the invention.

Other aims of the present invention will become directly apparent to the skilled man from the foregoing remarks and those that follow.

OBJECT OF THE INVENTION

In a first aspect the present invention relates to new substituted aryl-sulphonylamino-methylphosphonic acid derivatives of general formula

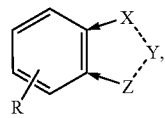

(I)

wherein
R denotes a group of formula

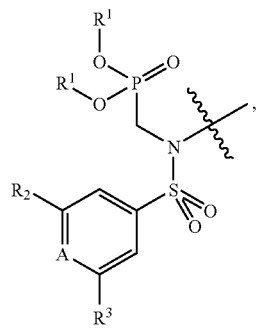

wherein
  $R^1$ denotes H, $C_{1-6}$-alkyl-carbonyl-oxy-$C_{1-3}$-alkyl or $C_{1-6}$-alkoxy-carbonyl-oxy-$C_{1-3}$-alkyl,
  $R^2$ and $R^3$ independently of one another denote H, halogen, $C_{1-3}$-alkyl, $C_{1-3}$-perfluoroalkyl, $C_{1-3}$-perfluoroalkoxy, $C_{1-3}$-alkoxy, cyano or nitro
  and
  A denotes CH or N,
and the heterocyclic group

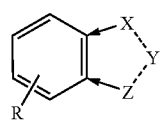

denotes a group of formula

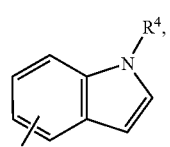

(Ia)

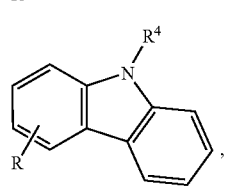

(Ib)

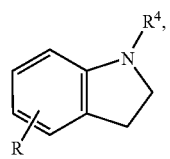

(Ic)

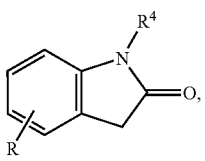 (Id)

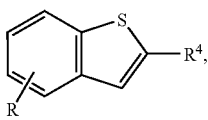 (Ie)

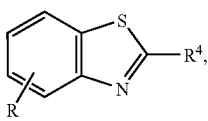 (If)

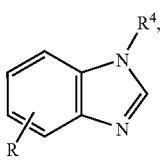 (Ig)

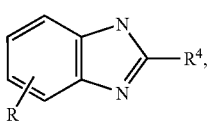 (Ih)

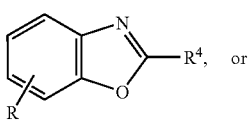 (Ii)

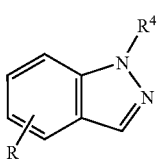 (Ij)

wherein the above-mentioned heterocycles of formulae (Ia), (Ic), (Id), (Ie), (Ig) and (Ij) may optionally be substituted at the carbon atoms of the 5 ring in each case by one or two groups selected from among halogen, $C_{1-3}$-alkyl, cyano, $C_{1-3}$-perfluoroalkyl, $C_{3-6}$-cycloalkyl, $C_{2-4}$-alkynyl, $C_{2-4}$-alkenyl, $C_{1-3}$-alkyl-carbonyl, $C_{1-3}$-perfluoroalkyl-carbonyl, carboxyl, aminomethyl, $C_{1-3}$-alkyl-aminomethyl, di-($C_{1-3}$-alkyl)-aminomethyl, aminocarbonyl, $C_{1-3}$-alkyl-aminocarbonyl or di-($C_{1-3}$-alkyl)-aminocarbonyl, wherein the groups are identical or different and each carbon atom can only carry one group, and wherein $R^4$ denotes a 1H-pyrimidin-2,4-dionyl or 2H-pyridazin-3-onyl group optionally mono- or disubstituted by one or two methyl groups or an optionally substituted aryl or heteroaryl group.

The invention also relates to the tautomers, stereoisomers, mixtures and salts, particularly the physiologically acceptable salts, of the compounds according to the invention.

The compounds of general formula I according to the invention and the physiologically acceptable salts thereof have valuable pharmacological properties, in particular they suppress the interaction of glycogen phosphorylase a with the $G_L$-subunit of glycogen-associated protein phosphatase 1 (PP1).

Therefore this invention also relates to the use of the compounds according to the invention, including the physiologically acceptable salts, as pharmaceutical compositions.

The compounds of the above general formula I, wherein $R^1$ does not represent hydrogen, but denotes one of the other groups specified, are so-called prodrugs. By prodrugs are meant compounds that are not active per se but are converted into the corresponding active compound in vivo, cleaving the prodrug group.

This invention further relates to pharmaceutical compositions containing at least one compound according to the invention or a physiologically acceptable salt according to the invention, optionally together with one or more inert carriers and/or diluents.

A further object of this invention is the use of at least one compound according to the invention or a physiologically acceptable salt of such a compound for preparing a pharmaceutical composition that is suitable for the treatment or prevention of diseases or conditions that can be influenced by suppressing the interaction of glycogen phosphorylase a with the $G_L$-subunit of glycogen-associated protein phosphatase 1 (PP1).

The invention also relates to the use of at least one compound according to the invention for preparing a pharmaceutical composition which is suitable for the treatment of metabolic disorders, for example type I or II diabetes mellitus.

The invention also relates to the use of at least one compound according to the invention for preparing a pharmaceutical composition for suppressing the interaction of glycogen phosphorylase a with the $G_L$-subunit of glycogen-associated protein phosphatase 1 (PP1).

A further object of this invention is a process for preparing a pharmaceutical composition according to the invention, characterised in that a compound according to the invention is incorporated in one or more inert carriers and/or diluents by a non-chemical method.

The present invention also relates to a process for preparing the compounds of general formula I according to the invention.

DETAILED DESCRIPTION OF THE INVENTION

Unless stated otherwise, the groups, radicals and substituents, particularly R, X, Y and Z, have the meanings given hereinbefore and hereinafter.

If groups, substituents or radicals occur more than once in a compound, they may have the same or different meanings.

Preferred compounds of the above general formula I are those wherein

R denotes a group of the above-mentioned formula wherein $R^1$ denotes H, $C_{1-6}$-alkyl-carbonyl-oxy-$C_{1-2}$-alkyl or $C_{1-6}$-alkoxy-carbonyl-oxy-$C_{1-2}$-alkyl $R^2$ and $R^3$ independently of one another denote halogen, $C_{1-3}$-alkyl, $C_{1-3}$-perfluoroalkyl, $C_{1-2}$-alkoxy or cyano and A denotes CH or N, and the heterocyclic group

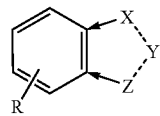

denotes a group of formula

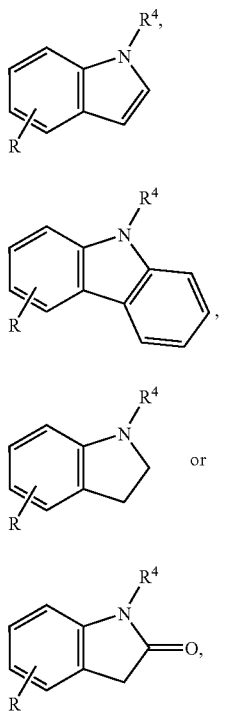

wherein the above-mentioned heterocycles of formulae (Ia), (Ic) and (Id) may optionally be substituted at the carbon atoms of the 5 ring by one or two groups selected from among halogen, $C_{1-3}$-alkyl, cyano, $C_{1-3}$-perfluoroalkyl, $C_{3-6}$-cycloalkyl, $C_{1-3}$-alkyl-carbonyl, $C_{1-3}$-perfluoroalkyl-carbonyl, aminocarbonyl, $C_{1-3}$-alkyl-aminocarbonyl or di-($C_{1-3}$-alkyl)-aminocarbonyl, while the groups are identical or different and each carbon atom carries at most one group, and wherein $R^4$ denotes a 1H-pyrimidin-2,4-dionyl or 2H-pyridazin-3-onyl group optionally mono- or disubstituted by one or two methyl groups or an optionally substituted aryl or heteroaryl group.

Particularly preferred are those compounds of the above general formula I, wherein R denotes a group of the above-mentioned formula, wherein $R^1$ denotes H, $C_{1-4}$-alkyl-carbonyl-oxy-$C_{1-2}$-alkyl or $C_{1-4}$-alkoxy-carbonyl-oxy-$C_{1-2}$-alkyl $R^2$ and $R^3$ independently of one another denote chlorine, bromine or $C_{1-2}$-alkyl and A denotes CH or N, and the heterocyclic group

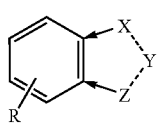

denotes a group of formula

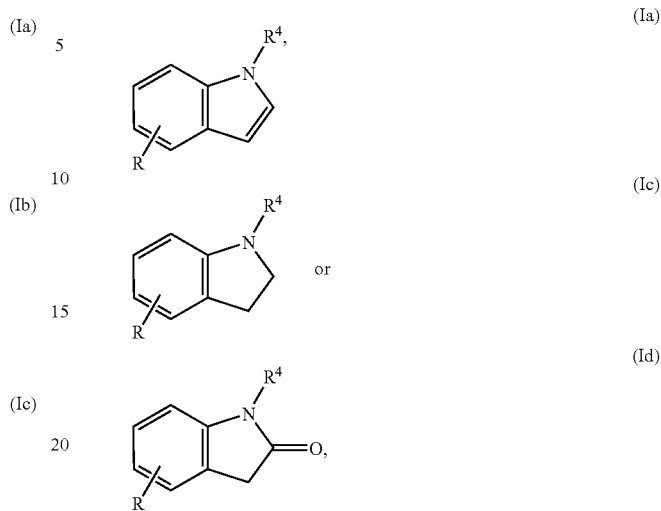

while the heterocyclic groups mentioned above may optionally be substituted at the carbon atoms of the 5 ring by a group selected from among chlorine, $C_{1-2}$-alkyl, cyano and trifluoromethyl, and wherein $R^4$ a 1H-pyrimidin-2,4-dionyl or 2H-pyridazin-3-onyl group optionally mono- or disubstituted by one or two methyl groups or an optionally substituted aryl or heteroaryl group;

but particularly those compounds of the above general formula I wherein

R denotes a group of the above-mentioned formula, wherein $R^1$ denotes H, tert.-butylcarbonyloxymethyl or iso-propyloxy-carbonyloxymethyl, $R^2$ and $R^3$ independently of one another denote chlorine, bromine or methyl and A denotes CH, and the heterocyclic group

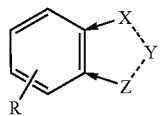

denotes a group of formula

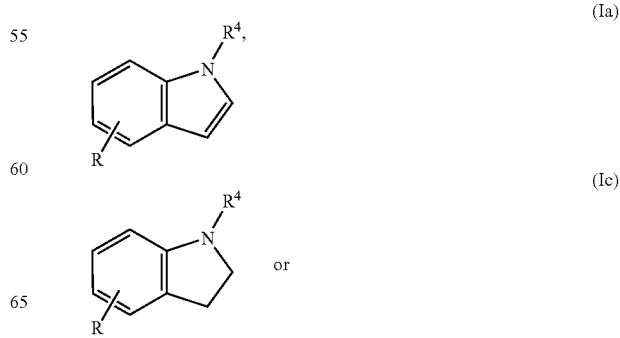

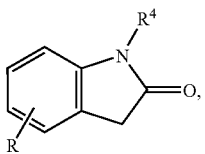

while the heterocyclic groups mentioned above may optionally be substituted at the carbon atom of the 5 ring adjacent to the phenyl ring by a methyl group or ethyl group and
$R^4$ denotes an optionally substituted aryl or heteroaryl group.

Most particularly preferred are those compounds of the above general formula I, wherein
R denotes a group of the above-mentioned formula, wherein
$R^1$ denotes H,
$R^2$ and $R^3$ in each case represent chlorine and
A denotes the group >CH,
and the heterocyclic group

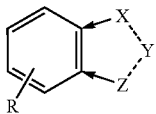

denotes a group of formula

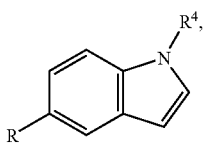

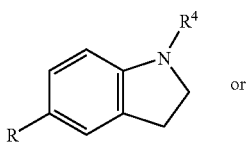
or

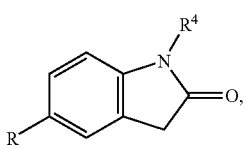

$R^4$ denotes an optionally substituted aryl or heteroaryl group.

Particular emphasis should be laid on the following compounds of general formula (I):
(1) {[(3,5-dichloro-phenylsulphonyl)-(1-pyrimidin-2-yl-2,3-dihydro-1H-indol-5-yl)-amino]-methyl}-phosphonic acid,
(2) {[[1-(2-chloro-phenyl)-2-oxo-2,3-dihydro-1H-indol-5-yl]-(3,5-dichloro-phenylsulphonyl)-amino]-methyl}-phosphonic acid,
(3) ({(3,5-dichloro-phenylsulphonyl)-[1-(2,6-dichloro-phenyl)-2-oxo-2,3-dihydro-1H-indol-5-yl]-amino}-methyl)-phosphonic acid,
(4) ({(3,5-dichloro-phenylsulphonyl)-[1-(1-methyl-1H-imidazol-2-yl)-2,3-dihydro-1H-indol-5-yl]-amino}-methyl)-phosphonic acid,
(5) ({(3,5-dichloro-phenylsulphonyl)-[1-(6-methyl-pyridazin-3-yl)-1H-indol-5-yl]-amino}-methyl)-phosphonic acid and
(6) [((3,5-dichloro-phenylsulphonyl)-{1-[6-(2-oxo-imidazolidin-1-yl)-pyridazin-3-yl]-1H-indol-5-yl}-amino)-methyl]-phosphonic acid,
as well as the enantiomers thereof, the mixtures thereof and the salts thereof.

Some terms used hereinbefore and hereinafter to describe the compounds according to the invention are defined more specifically below.

The term halogen denotes an atom selected from among F, Cl, Br and I, particularly F, Cl and Br.

The term $C_{1-n}$-alkyl, wherein n may have a value as defined hereinbefore or hereinafter, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{2-n}$-alkynyl, wherein n may have a value as defined hereinbefore, denotes a branched or unbranched hydrocarbon group with 2 to n C atoms and a C≡C-triple bond. Examples of such groups include ethynyl, 1-propynyl, 2-propynyl, iso-propynyl, 1-butynyl, 2-butynyl, 3-butynyl, 2-methyl-1-propynyl, 1-pentynyl, 2-pentynyl, 3-pentynyl, 4-pentynyl, 3-methyl-2-butynyl, 1-hexynyl, 2-hexynyl, 3-hexynyl, 4-hexynyl, 5-hexynyl etc.

The term $C_{2-n}$-alkenyl, wherein n may have a value as defined hereinbefore, denotes a branched or unbranched hydrocarbon group with 2 to n C atoms and a C═C-double bond. Examples of such groups include ethenyl, 1-propenyl, 2-propenyl, iso-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl etc.

The term $C_{1-n}$-alkoxy or $C_{1-n}$-alkyloxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkyl-carbonyl denotes a $C_{1-n}$-alkyl-C(═O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neopentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbornyl, norcaryl, adamantyl, etc. Preferably the term $C_{3-7}$-cycloalkyl includes saturated monocyclic groups.

The term $C_{3-n}$-cycloalkyloxy or $C_{3-n}$-cycloalkoxy d a $C_{3-n}$-cycloalkyl-O group, wherein $C_{3-n}$-cycloalkyl is as hereinbefore defined. Examples of such groups include cyclopropyloxy, cyclobutyloxy, cyclopentyloxy, cyclohexyloxy, cycloheptyloxy, etc.

The term $C_{1-n}$-alkoxy-carbonyl denotes a $C_{1-n}$-alkyl-O—C(═O) group, wherein $C_{1-n}$-alkyl is as hereinbefore defined.

The term $C_{3-n}$-cycloalkyl-carbonyl denotes a $C_{3-n}$-cycloalkyl-C(═O) group, wherein $C_{3-n}$-cycloalkyl is as hereinbefore defined.

The terms $C_{1-n}$-alkyl-amino and di-($C_{1-n}$-alkyl)-amino denote a $C_{1-n}$-alkyl-NH— or a di-($C_{1-n}$-alkyl)-N group, respectively, wherein $C_{1-n}$-alkyl is as hereinbefore defined.

The term $C_{3-n}$-cycloalkyl-amino denotes a $C_{3-n}$-cycloalkyl-NH group, wherein $C_{3-n}$-cycloalkyl is as hereinbefore defined.

The term N—($C_{3-n}$-cycloalkyl)-N—($C_{1-n}$-alkyl)-amino denotes an N—($C_{3-n}$-cycloalkyl)-N—($C_{1-n}$-alkyl)-N group, wherein $C_{3-n}$-cycloalkyl and $C_{1-n}$-alkyl are as hereinbefore defined.

The terms $C_{1-n}$-alkyl-aminocarbonyl and di-($C_{1-n}$-alkyl)-aminocarbonyl denote a $C_{1-n}$-alkyl-NH—C(=O)— or a di-($C_{1-n}$-alkyl)-N—C(=O) group, respectively, wherein $C_{1-n}$-alkyl is as hereinbefore defined.

The term $C_{3-n}$-cycloalkyl-aminocarbonyl denotes a $C_{3-n}$-cycloalkyl-NH—C(=O) group, wherein $C_{3-n}$-cycloalkyl is as hereinbefore defined.

The term N—($C_{3-n}$-cycloalkyl)-N—($C_{1-n}$-alkyl)-amino denotes an N—($C_{3-n}$-cycloalkyl)-N—($C_{1-n}$-alkyl)-N—C(=O) group, wherein $C_{3-n}$-cycloalkyl and $C_{1-n}$-alkyl are as hereinbefore defined.

The terms di-($C_{1-n}$-alkyl)amino and di-($C_{1-n}$-alkyl)aminocarbonyl, wherein n has a value as defined hereinbefore, encompass amino groups which have the same or two different alkyl groups.

The term $C_{1-n}$-perfluoroalkyl denotes a F—(CF2)$_n$ group. Examples of such groups include trifluoromethyl, pentafluoroethyl, heptafluoro-n-propyl, heptafluoro-iso-propyl etc., but preferably trifluoromethyl, pentafluoroethyl.

The term $C_{1-n}$-perfluoroalkoxy denotes a F—(CF2)$_n$-O group. Examples of such groups include trifluoromethoxy, pentafluoroethoxy, heptafluoro-n-propoxy, heptafluoro-iso-propoxy etc., but preferably trifluoromethoxy, pentafluoroethoxy.

The term $C_{1-n}$-alkylsulphanyl denotes a $C_{1-n}$-alkyl-S group, wherein $C_{1-n}$-alkyl is as hereinbefore defined.

The term $C_{1-n}$-alkylsulphinyl denotes a $C_{1-n}$-alkyl-S(=O) group, wherein $C_{1-n}$-alkyl is as hereinbefore defined.

The term $C_{1-n}$-alkylsulphonyl denotes a $C_{1-n}$-alkyl-S(=O)$_2$ group, wherein $C_{1-n}$-alkyl is as hereinbefore defined.

The term $C_{3-n}$-cycloalkylsulphanyl denotes a $C_{3-n}$-cycloalkyl-S group, wherein $C_{3-n}$-cycloalkyl is as hereinbefore defined.

The term $C_{3-n}$-cycloalkylsulphinyl denotes a $C_{3-n}$-cycloalkyl-S(=O) group, wherein $C_{3-n}$-cycloalkyl is as hereinbefore defined.

The term $C_{3-n}$-cycloalkylsulphonyl denotes a $C_{3-n}$-cycloalkyl-S(=O)$_2$ group, wherein $C_{3-n}$-cycloalkyl is as hereinbefore defined.

Among the optionally substituted aryl or heteroaryl groups mentioned above for $R^4$ are included a phenyl or naphthyl group, wherein one to three methyne groups may each be replaced by a nitrogen atom, or a thiazolyl, thiadiazolyl, pyrazolyl or imidazolyl group, which may be mono-, di- or trisubstituted in each case by halogen, cyano, trifluoromethyl or hydroxy, $C_{1-4}$-alkyloxy, which may optionally be substituted from position 2 by a hydroxy, amino, $C_{1-4}$-alkyl-amino or di-($C_{1-3}$-alkyl)-amino group, $C_{3-7}$-cycloalkyl, $C_{3-7}$-cycloalkyloxy or $C_{3-7}$-cycloalkylamino, while in the 5 to 7-membered cycloalkyl moieties in each case a methylene group may be replaced by an oxygen atom, $C_{1-4}$-alkyl, which may be substituted by an amino or hydroxy group, amino, $C_{1-4}$-alkyl-amino, di-($C_{1-3}$-alkyl)-amino, $C_{1-3}$-alkyl-carbonylamino or $C_{3-7}$-cycloalkyl-amino, while the $C_{1-4}$-alkyl-amino- and di-($C_{1-3}$-alkyl)-amino groups in the alkyl moiety may each be substituted from position 2 by a hydroxy, amino, $C_{1-4}$-alkyl-amino, di-($C_{1-3}$-alkyl)-amino, $C_{1-3}$-alkyl-carbonylamino or $C_{1-3}$-alkyl-sulphonylamino group, aminocarbonyl, ($C_{1-3}$-alkyl-amino)-carbonyl, [di-($C_{1-3}$-alkyl)-amino]-carbonyl, $C_{3-7}$-cycloalkyl-aminocarbonyl, $C_{1-3}$-alkyl-carbonyl or $C_{1-4}$-alkoxy-carbonyl, $C_{1-3}$-alkylsulphonyl, $C_{1-3}$-alkylsulphinyl or $C_{1-3}$-alkylsulphanyl, oxazolyl, thiazolyl, oxoimidazolidinyl or imidazolyl, which may optionally be substituted by a $C_{1-3}$-alkyl group, or a 5- to 7-membered cycloalkyleneimino group wherein a methyne group may be replaced by an oxygen or sulphur atom or by an —NH, —N($C_{1-3}$-alkylsulphonyl) or —N($C_{1-3}$-alkyl-carbonyl)-group r and optionally a further methyne group may be replaced by a carbonyl, sulphinyl or sulphonyl group, while the substituents may be identical or different;

the group in question preferably being a phenyl, pyridinyl, pyrimidinyl, pyrazinyl, pyridazinyl, triazinyl, thiazolyl, thiadiazolyl, pyrazolyl or imidazolyl group, which may be mono- or disubstituted in each case by chlorine, bromine, cyano or trifluoromethyl, $C_{1-4}$-alkyloxy, which may optionally be substituted from position 2 by a hydroxy, amino, $C_{1-4}$-alkyl-amino or di-($C_{1-3}$-alkyl)-amino group, $C_{5-7}$-cycloalkyloxy or $C_{5-7}$-cycloalkylamino, while in the 5- to 7-membered cycloalkyl moieties a methylene group is replaced in each case by an oxygen atom, $C_{1-4}$-alkyl, which may be substituted by an amino or hydroxy group, amino, $C_{1-4}$-alkyl-amino, di-($C_{1-3}$-alkyl)-amino, $C_{1-3}$-alkyl-carbonylamino or $C_{3-5}$-cycloalkyl-amino, while the $C_{1-4}$-alkyl-amino- and di-($C_{1-3}$-alkyl)-amino groups in the alkyl moiety may be substituted in each case from position 2 by a hydroxy, amino, $C_{1-4}$-alkyl-amino, di-($C_{1-3}$-alkyl)-amino, $C_{1-3}$-alkyl-carbonylamino or $C_{1-3}$-alkyl-sulphonylamino group, aminocarbonyl, ($C_{1-3}$-alkyl-amino)-carbonyl, [di-($C_{1-3}$-alkyl)-amino]-carbonyl, $C_{3-5}$-cycloalkyl-aminocarbonyl, $C_{1-3}$-alkyl-carbonyl or $C_{1-4}$-alkoxy-carbonyl, $C_{1-3}$-alkylsulphonyl, $C_{1-3}$-alkylsulphinyl or $C_{1-3}$-alkylsulphanyl, oxazolyl, thiazolyl, oxoimidazolidinyl or imidazolyl, which may optionally be substituted by a $C_{1-3}$-alkyl group, or a 5- to 7-membered cycloalkyleneimio group wherein a methyne group may be replaced by an oxygen or sulphur atom or by an —NH, —N($C_{1-3}$-alkylsulphonyl) or —N($C_{1-3}$-alkylcarbonyl) group and optionally a further methyne group is replaced by a carbonyl, sulphinyl or sulphonyl group, while the substituents may be identical or different;

particularly preferred is a phenyl, pyridinyl, pyrimidinyl, pyrazinyl, pyridazinyl or imidazolyl group, which may be substituted in each case by one or two substituents selected from chlorine, methyl, ethyl, isopropyl, amino, methylamino, dimethylamino, aminocarbonyl, methylaminocarbonyl, dimethylaminocarbonyl, methylsulphonyl, methylsulphinyl, methylsulphanyl, 2-oxo-imidazolidinyl, morphonin-4-yl, piperazin-1-yl and 4-methyl-piperazin-1-yl,
while the substituents may be identical or different;
most particularly preferred is a phenyl, pyrimidinyl, pyridazinyl or imidazolyl group, which may be substituted in each case by one or two chlorine atoms or a methyl or 2-oxo-imidazolidinyl group;
but particular mention should be made of pyrimidin-2-yl, 2-chlorophenyl, 2,6-dichlorophenyl, 1-methyl-imidazol-2-yl, 6-methyl-pyridazin-3-yl and 6-(2-oxo-imidazolidin-1-yl)-pyridazin-3-yl.

The compounds according to the invention may be obtained using methods of synthesis that are known in principle. Preferably the compounds are obtained by the methods of preparation according to the invention that are described more fully hereinafter.

Compounds of general formula I may be prepared according to Process a) shown in Scheme 1, wherein X, Y, Z, $R^1$, $R^2$, $R^3$ and A are as hereinbefore defined, starting from a compound of general formula II.

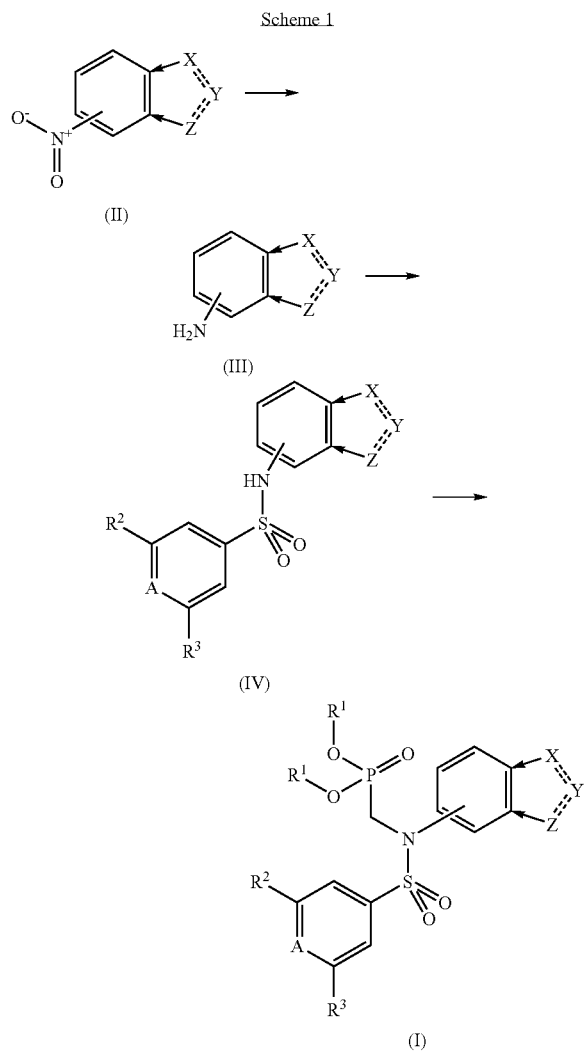

Compounds of general formula III are obtained by reacting a compound of general formula II with a reducing agent.

A suitable reducing agent, for example, is hydrogen in the presence of a catalyst, such as palladium on charcoal, palladium hydroxide on charcoal or Raney nickel, while palladium on charcoal is particularly suitable. The hydrogenation is carried out in a suitable solvent, such as methanol, ethanol, isopropanol, tetrahydrofuran, dichloromethane or ethyl acetate, but preferably methanol, ethanol or tetrahydrofuran, at a pressure between 0.5 and 7 bar, but preferably at a pressure between 0.5 and 3 bar, and at a temperature between 0° C. and 60° C., but preferably at a temperature between 15° C. and 40° C.

Also suitable for the reduction is tin dichloride hydrate in lower alcoholic solvents such as methanol or ethanol at a temperature between ambient temperature and 80° C.

Alternatively titanium trichloride may be used as the reducing agent. Solvents used may be mixtures of acetone and water. The reaction is carried out between 0° C. and 60° C., but preferably between 15° C. and 40° C. and in the presence of ammonium acetate.

Compounds of general formula IV are obtained by sulphonylation of compounds of general formula III.

The sulphonylation is carried out with aromatic sulphonyl chlorides in the presence of a base such as triethylamine, N,N-diisopropyl-N-ethyl-amine, pyridine, or 4-dimethylamino-pyridine, but preferably pyridine. The reaction may be carried out in suitable solvents, such as diethyl ether, tetrahydrofuran, toluene, pyridine, dichloromethane, or chloroform, but preferably dichloromethane. The temperature may be between 0° C. and 60° C., but preferably between 15° C. and 40° C.

Compounds of general formula I are obtained from compounds of general formula IV by alkylation.

Suitable alkylating agents are methylphosphonic acid ester derivatives which contain at the methyl group a leaving group such as chlorine, bromine, iodine, p-tolylsulphonate, methylsulphonate or trifluoromethylsulphonate. The alkylation is carried out in a solvent such as dimethylformamide, dimethylacetamide, tetrahydrofuran, acetonitrile, N-methylpyrrolidone or dimethylsulphoxide, but preferably in dimethylformamide, in the presence of a base such as sodium carbonate, potassium carbonate or caesium carbonate, but preferably potassium carbonate, and at a temperature between 0° C. and 100° C., but preferably between 15° C. and 50° C.

If methyl phosphonate derivatives with ethyl phosphonate groups are used as alkylating agents, compounds of general formula I are obtained wherein $R^1$=ethyl. The ethyl groups therein are preferably cleaved by treating with trimethylsilyl-bromide or trimethylsilyl iodide in dichloromethane or 1,2-dichloroethane.

Compounds of general formula II wherein $R^4$ is bound to X and X denotes nitrogen may be obtained by process b) shown in Scheme 2 from compounds of general formula V wherein —Y . . . Z→ denotes —CH═CH→ or —CH$_2$—CH$_2$→, while the carbon atoms therein may be substituted as hereinbefore defined and $R^4$ denotes an aryl group.

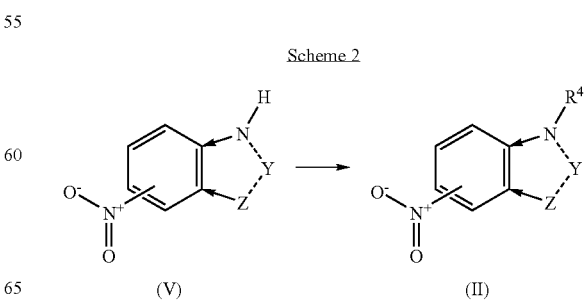

Aryl groups may be introduced by reacting with nitrogen-containing aromatic groups which contain, at the carbon atom adjacent to the nitrogen, a leaving group such as fluorine, chlorine, bromine, iodine, alkylsulphanyl, arylsulphanyl, alkylsulphinyl, arylsulphinyl, alkylsulphonyl or arylsulphonyl, but preferably chlorine, bromine or iodine. The reaction may be carried out without a solvent, at temperatures between 70° C. and 220° C., but preferably between 120° C. and 190° C.

Alternatively the reaction may be carried out in a dipolar-aprotic solvent such as dimethylformamide, dimethylacetamide, tetrahydrofuran, acetonitrile, N-methylpyrrolidone or dimethylsulphoxide, but preferably in dimethylformamide or N-methylpyrrolidone, in the presence of a base such as triethylamine, N,N-diisopropyl-N-ethyl-amine, sodium carbonate, potassium carbonate, caesium carbonate, sodium hydride, potassium-tert.-butoxide or potassium-hexamethyl-disilazide, but preferably sodium hydride, potassium carbonate or potassium-tert.-butoxide, and at a temperature between 0° C. and 150° C., but preferably between 15° C. and 100° C.

The arylation reaction may also be carried out for compounds of general formula V wherein —Y . . . Z→ denotes —CH=CH→, while the carbon atoms therein may be substituted as hereinbefore defined, according to the process described in *J. Am. Chem. Soc.* 2002, 124, 11684-11688, to obtain compounds of general formula II wherein —Y . . . Z→ denotes —CH=CH→, while the carbon atoms therein may be substituted as hereinbefore defined.

Compounds of general formula V are reacted with arylbromides or aryliodides. The reaction is carried out in toluene or dioxane in the presence of potassium phosphate as base, catalytic amounts of a copper-(I) salt, but preferably copper-(I)-iodide and catalytic amounts of a 1,2-diamino ligand such as for example ethylenediamine, N,N-ethylenediamine, N,N'-ethylenediamine, cis-cyclohexane-1,2-diamine, trans-cyclohexane-1,2-diamine, N,N'-dimethyl-cis-cyclohexane-1,2-diamine or N,N'-dimethyl-trans-cyclohexane-1,2-diamine, but preferably N,N'-dimethyl-trans-cyclohexane-1,2-diamine, at a temperature between 70° C. and 130° C., but preferably between 90° C. and 110° C.

End compounds of general formula VII which contain an indole scaffold may be obtained according to Process c) according to the invention shown in Scheme 3, wherein $R^1$, $R^2$, $R^3$ and A are as hereinbefore defined and the carbon atoms of the 5 ring may be substituted as hereinbefore defined, from compounds of general formula VI.

Scheme 3

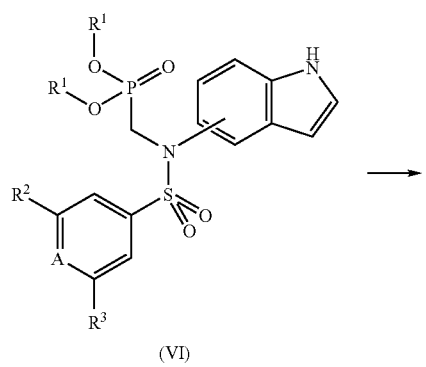

(VI)

-continued

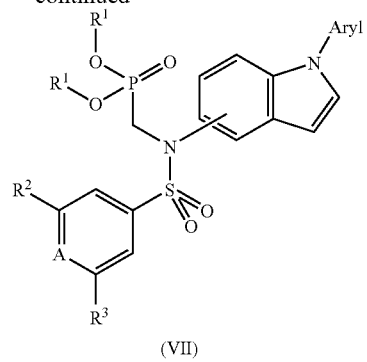

(VII)

The arylation reaction is carried out according to methods known from the literature, as described for example in *J. Am. Chem. Soc.* 2002, 124, 11684-11688. Compounds of general formula V are reacted with arylbromides or aryliodides. The reaction is carried out in toluene or dioxane in the presence of potassium phosphate as base, catalytic amounts of a copper-(I) salt, but preferably copper-(I)-iodide and catalytic amounts of a 1,2-diamino ligand such as for example ethylenediamine, N,N-ethylenediamine, N,N'-ethylenediamine, cis-cyclohexane-1,2-diamine, trans-cyclohexane-1,2-diamine, N,N'-dimethyl-cis-cyclohexane-1,2-diamine or N,N'-dimethyl-trans-cyclohexane-1,2-diamine, but preferably N,N'-dimethyl-trans-cyclohexane-1,2-diamine, at a temperature between 70° C. and 130° C., but preferably between 90° C. and 110° C.

If compounds of general formula VI wherein $R^1$=ethyl are used, compounds of general formula VII are obtained wherein $R^1$=ethyl. The ethyl groups therein are preferably cleaved by treating with trimethylsilyl bromide or trimethylsilyl iodide in dichloromethane or 1,2-dichloroethane.

Central scaffold components of general formulae II or III which are not commercially obtainable may be obtained by methods known from the literature. Indoles, for example, may be obtained by converting 4-nitrophenyl-hydrazine into a hydrazone and then carrying out Fischer indole synthesis as described in *Organic Preparations and Procedures International* 1991, 23(3), 357-363. Alternatively, indole components may be obtained starting from substituted 4-nitroanilines analogously to a procedure as described in *Tetrahedron* 2003, 59, 1571-1587. The starting compounds of general formula II may also be prepared by nitrogenation (Houben-Weyl, *Methoden der organischen Chemie*, volume X/1, 463-890) using methods known per se starting from commercially obtainable compounds.

Cyano functionalities may in each case be prepared from primary amides obtained in the syntheses. Suitable methods for this transformation are, for example, reaction with thionyl chloride and optionally catalytic amounts of dimethylformamide in a solvent such as dichloromethane, 1,2-dichloroethane, toluene or acetone at temperatures between 0° C. and 100° C., reaction with trifluoroacetic anhydride or trichloroacetic anhydride, a base such as for example pyridine, triethylamine or N,N-diisopropyl-N-ethyl-amine in a solvent such as for example dichloromethane, 1,2-dichloroethane, tetrahydrofuran, 1,4-dioxane or toluene at temperatures between −10° C. and 100° C., as well as reaction with phosphorus oxychloride and optionally a base such as pyridine or N,N-dimethylaniline in the presence or absence of a solvent such as for example dichloromethane, 1,2-dichloroethane, tetrahydrofuran, 1,4-dioxane or toluene, at temperatures between −10° C. and 120° C.

In the reactions described hereinbefore, any reactive groups present such as carboxy, hydroxy, amino or alkylamino groups may be protected during the reaction by conventional protecting groups which are cleaved again after the reaction.

For example, a protecting group for a carboxy group may be a methyl, ethyl, tert.butyl or benzyl group.

For example, a protecting group for a hydroxy group may be an acetyl, benzyl or tetrahydropyranyl group.

Protecting groups for an amino or alkylamino may be a formyl, acetyl, trifluoroacetyl, ethoxycarbonyl, tert.butoxycarbonyl, benzyloxycarbonyl, benzyl, methoxybenzyl or 2,4-dimethoxybenzyl group.

A carboxymethyl or carboxyethyl unit is cleaved for example by hydrolysis in an aqueous solvent, e.g. in water, methanol/water, isopropanol/water, acetic acid/water, tetrahydrofuran/water or dioxane/water, but preferably in methanol/water, in the presence of an acid such as trifluoroacetic acid, hydrochloric acid or sulphuric acid or in the presence of an alkali metal base such as lithium hydroxide, sodium hydroxide or potassium hydroxide, but preferably sodium hydroxide, or aprotically, e.g. in the presence of iodotrimethylsilane, at temperatures between 0 and 120° C., preferably at temperatures between 10 and 100° C.

A benzyl, methoxybenzyl or benzyloxycarbonyl group is advantageously cleaved by hydrogenolysis, e.g. with hydrogen in the presence of a catalyst such as palladium on charcoal in a suitable solvent such as methanol, ethanol, ethyl acetate or glacial acetic acid, optionally with the addition of an acid such as hydrochloric acid, at temperatures between 0 and 100° C., but preferably at temperatures between 20 and 60° C., and under a hydrogen pressure of 1 to 7 bar, but preferably 1 to 3 bar. However, a 2,4-dimethoxy-benzyl group is preferably cleaved in trifluoroacetic acid in the presence of anisole.

A tert.-butyl or tert.-butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethyl ether.

Moreover, the compounds of general formula I obtained, or intermediate products from the synthesis of compounds of general formula I, as already mentioned hereinbefore, may be resolved into their enantiomers and/or diastereomers. Thus, for example, cis/trans mixtures may be resolved into their cis and trans isomers, and compounds with at least one stereocentre may be resolved into their enantiomers.

Thus, for example, the cis/trans mixtures may be resolved by chromatography into the cis and trans isomers thereof, the compounds of general formula I obtained, or intermediate products from the synthesis of compounds of general formula I, which occur as racemates may be separated by methods known per se (cf. Allinger N. L. and Eliel E. L. in "Topics in Stereochemistry", Vol. 6, Wiley Interscience, 1971) into their optical antipodes and compounds of general formula I, or intermediate products from the synthesis of compounds of general formula I, with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by chromatography on chiral phases or by recrystallisation from an optically active solvent or by reacting with an optically active substance which forms salts or derivatives such as e.g. Esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-O-p-toluoyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I obtained, or intermediate products from the synthesis of compounds of general formula I, may be converted into the salts thereof, particularly for pharmaceutical use into the physiologically acceptable salts thereof with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the new compounds of general formula I obtained, or intermediate products from the synthesis of compounds of general formula I, if they contain a carboxy group, may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formula I are inhibitors of the interaction between human liver glycogen phosphorylase (HLGP) and protein PPP1R3 ($G_L$-subunit of glycogen-associated protein phosphatase 1 (PP1)). The effect of the compounds on the binding of the protein PPP1R3 and the glycogen phosphorylase activated by phosphorylation is determined in a binding test based on SPA technology (Amersham Pharmacia). The binding of the substances inhibits the interaction of the glycogen phosphorylase with the protein PPP1R3B. All measurements were made in triplicate in the 384-well format (Optiplate, Perkin Elmer).

Human glycogen phosphorylase is recombinantly expressed in *E. Coli* and purified. The isolated non-phosphorylated HLGP is radioactively labelled in a marking reaction with phosphorylase kinase (200-500 U/mg, P2014, Sigma) and $^{33}$P-gamma ATP (110 TBq/mmol, Hartmann Analytic) (Ref.: Cohen et al., Methods Enzymol. 1988, Vol 159 pp 390). In a binding test, in a volume of 100 µl (test buffer: 50 mM Tris/HCl pH 7.0, 0.1 mM EGTA, 0.1% mercapto-ethanol), different amounts of a test substance (final concentration: 1 nM to 30 µM) are incubated at ambient temperature for 16 hours with 100000 cpm of labelled HLGP, 375 µg streptavidin-SPA Beads (RPNQ 0007, Amersham Pharmacia), 0.1 µg GL-peptide (Biotin-FPEWPSYLGYEKLGPYY). After centrifuging for 5 minutes at 500 g the plate is measured (Topcount, Packard). The cpm values measured are used to calculate the $IC_{50}$ values specified. The basal value is determined in the absence of the peptide and the maximum value is determined in the absence of the test substance.

The compounds of general formula I have $IC_{50}$ values in the range from 30 nM to 1.3 µM.

In view of their ability to suppress the interaction of glycogen phosphorylase a with the GL-subunit of glycogen-associated protein phosphatase 1 (PP1), the compounds of general formula I according to the invention and the corresponding pharmaceutically acceptable salts thereof are theoretically suitable for treating and/or preventatively treating all those conditions or diseases that can be influenced by inhibiting the interaction of glycogen phosphorylase a with the GL-subunit of glycogen-associated protein phosphatase 1 (PP1). Therefore the compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia. These substances are also suitable for preventing beta-cell degeneration such as e.g. apoptosis or necrosis of pancreatic beta cells. The substances are also suitable for improving or restoring the functionality of pancreatic cells, and also for increasing the number and size of pancreatic beta cells. The compounds according to the invention may also be used as diuretics or antihypertensives and are suitable for the prevention and treatment of acute renal failure.

In particular, the compounds according to the invention, including the physiologically acceptable salts thereof, are suitable for the prevention or treatment of diabetes, particularly type 1 and type 2 diabetes mellitus, and/or diabetic complications.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 0.1 to 1000 mg, preferably 0.5 to 500 mg, by intravenous route, and 1 to 1000 mg, preferably 10 to 500 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include in particular those which potentiate the therapeutic effect of an inhibitor of the interaction of glycogen phosphorylase a with the $G_L$ subunit of glycogen-associated protein phosphatase 1 (PP1) according to the invention with respect to one of the indications mentioned and/or which allow the dosage of an inhibitor of the interaction of glycogen phosphorylase a with the GL subunit of glycogen-associated protein phosphatase 1 (PP1) according to the invention to be reduced. Therapeutic agents which are suitable for such a combination include, for example, antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. Miglitol, acarbose, voglibose), DPPIV inhibitors (e.g. e.g. sitagliptine, vildagliptine), SGLT2-inhibitors, alpha2-antagonists, insulin and insulin analogues, GLP-1 and GLP-1 analogues (e.g. Exendin-4) or amylin. Other active substances suitable as combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully 1/5 of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the interaction of glycogen phosphorylase a with the $G_L$ subunit of glycogen-associated protein phosphatase 1 (PP1). These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

In the foregoing and following text, H atoms of hydroxyl groups are not explicitly shown in every case in structural formulae. The Examples that follow are intended to illustrate the present invention without restricting it:

PREPARATION OF THE STARTING COMPOUNDS

Example I

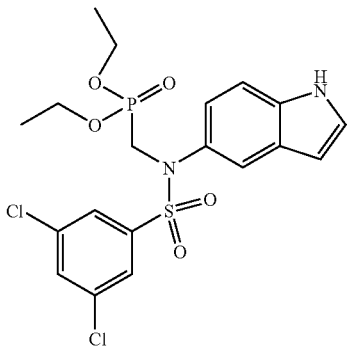 [SMILES: CCOP(=O)(CN(c1ccc2[nH]ccc2c1)S(=O)(=O)c1cc(Cl)cc(Cl)c1)OCC]

Diethyl {[(3,5-dichloro-phenylsulphonyl)-(1H-indol-5-yl)-amino]-methyl}-phosphonate 2.56 g 3,5-dichloro-N-(1H-indol-5-yl)-phenylsulphonamide are dissolved in 25 ml dimethylformamide. To this, 3.11 g potassium carbonate and 2.93 ml diethoxy-phosphorylmethyl trifluoro-methanesulphonate are added dropwise. The mixture is stirred overnight at ambient temperature, divided between water and ethyl acetate and the aqueous phase is extracted twice with ethyl acetate. The combined organic phases are washed twice with water and once with saturated sodium chloride solution and dried on magnesium sulphate. The solvents are eliminated in vacuo, the residue is dissolved in hot ethyl acetate and after cooling to ambient temperature the precipitated solid is suction filtered. Further product is obtained by freeing the mother liquor in vacuo from the volatile constituents and chromatographing the residue on silica gel (cyclohexane/ethyl acetate 50:50 to 25:75).

Yield: 3.6 g (98% of theory)
Mass spectrum (ESI$^+$): m/z=491 [M+H]$^+$
$R_f$ value: 0.30 (silica gel, petroleum ether/ethyl acetate 1:2)

The following compounds are obtained analogously to Example I:

(1) diethyl {[[1-(2-chloro-phenyl)-2-oxo-2,3-dihydro-1H-indol-5-yl]-(3,5-dichloro-phenylsulphonyl)-amino]-methyl}-phosphonate

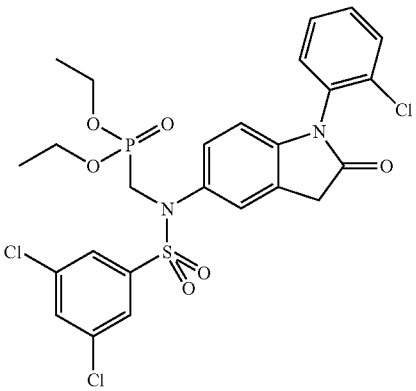 [SMILES: CCOP(=O)(CN(c1ccc2c(c1)CC(=O)N2c1ccccc1Cl)S(=O)(=O)c1cc(Cl)cc(Cl)c1)OCC]

and diethyl ({(3,5-dichloro-phenylsulphonyl)-[1-(2,6-dichloro-phenyl)-2-oxo-2,3-dihydro-1H-indol-5-yl]-amino}-methyl)-phosphonate

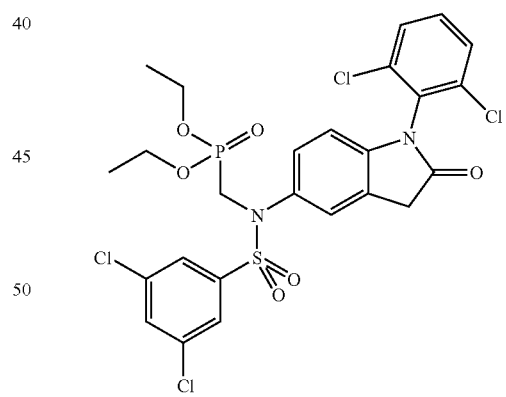

are obtained by reacting a mixture of 3,5-dichloro-N-[1-(2-dichloro-phenyl)-2-oxo-2,3-dihydro-1H-indol-5-yl]-phenylsulphonamide and 3,5-dichloro-N-[1-(2,6-dichloro-phenyl)-2-oxo-2,3-dihydro-1H-indol-5-yl]-phenylsulphonamide. The products are separated by chromatography on silica gel.

Mass spectrum (ESI$^+$): m/z=617 [M+H]$^+$ diethyl {[[1-(2-chloro-phenyl)-2-oxo-2,3-dihydro-1H-indol-5-yl]-(3,5-dichloro-phenylsulphonyl)-amino]-methyl}-phosphonate and Mass spectrum (ESI$^+$): m/z=651 [M+H]$^+$ diethyl ({(3,5-dichloro-phenylsulphonyl)-[1-(2,6-dichloro-phenyl)-2-oxo-2,3-dihydro-1H-indol-5-yl]-amino}-methyl)-phosphonate (2) diethyl {[(3,5-dichloro-phenylsulphonyl)-(1-pyrimidin-2-yl-2,3-dihydro-1H-indol-5-yl)-amino]-methyl}-phosphonate

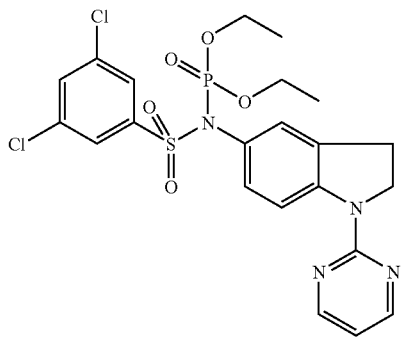 [SMILES: CCOP(=O)(OCC)N(c1ccc2c(c1)CCN2c1ncccn1)S(=O)(=O)c1cc(Cl)cc(Cl)c1]

The crude product is purified by chromatography on silica gel.

Mass spectrum (ESI⁺): m/z=573 [M+H]⁺

(3) diethyl ({(3,5-dichloro-phenylsulphonyl)-[1-(1-methyl-1H-imidazol-2-yl)-2,3-dihydro-1H-indol-5-yl]-amino}-methyl)-phosphonate

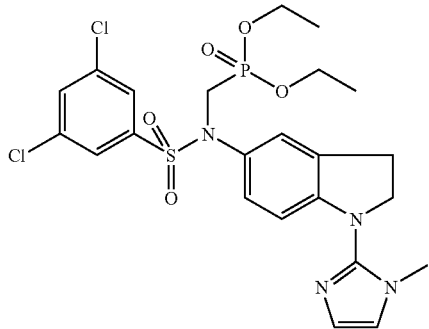 [SMILES: CCOP(=O)(CN(c1ccc2c(c1)CCN2c1nccn1C)S(=O)(=O)c1cc(Cl)cc(Cl)c1)OCC]

$R_f$ value: 0.22 (silica gel, petroleum ether/ethyl acetate 1:4)

Example II

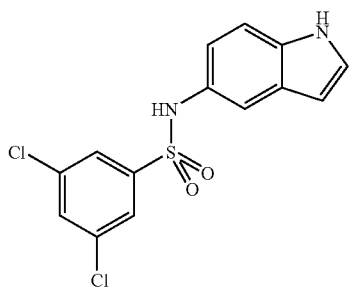 [SMILES: O=S(=O)(Nc1ccc2[nH]ccc2c1)c1cc(Cl)cc(Cl)c1]

3,5-dichloro-N-(1H-indol-5-yl)-phenylsulphonamide 2.5 g 5-aminoindole are dissolved in 25 ml of pyridine. To this are added 4.64 g of 3,5-dichlorophenylsulphonyl chloride and the mixture is stirred for 4 hours at ambient temperature. The solvent is eliminated in vacuo and the residue is divided between water and ethyl acetate. The aqueous phase is extracted with ethyl acetate and the combined organic phases are washed with saturated sodium chloride solution. After drying with magnesium sulphate the solvents are eliminated in vacuo and the residue is chromatographed on silica gel (cyclohexane/ethyl acetate 10:1 to 1:5).

Yield: 6 g (93% of theory)

Mass spectrum (ESI⁺): m/z=341 [M+H]⁺

The following compounds are obtained analogously to Example II:

(1) 3,5-dichloro-N-[1-(2,6-dichloro-phenyl)-2-oxo-2,3-dihydro-1H-indol-5-yl]-phenylsulphonamide

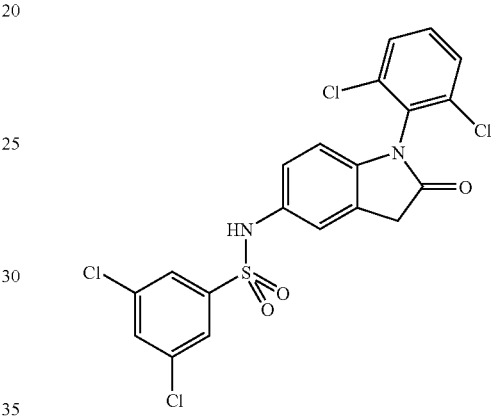

and 3,5-dichloro-N-[1-(2-chloro-phenyl)-2-oxo-2,3-dihydro-1H-indol-5-yl]-phenylsulphonamide

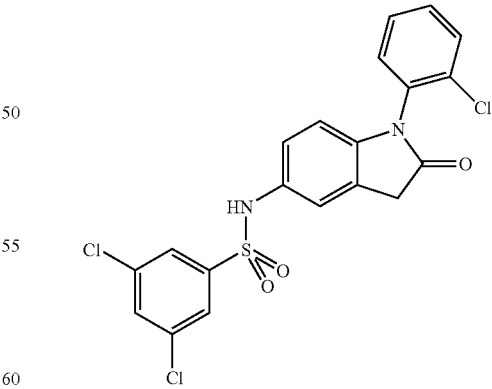

are obtained as a mixture by reacting a mixture of 5-amino-1-(2,6-dichloro-phenyl)-1,3-dihydro-indol-2-one and 5-amino-1-(2-chloro-phenyl)-1,3-dihydro-indol-2-one. The product mixture is further reacted directly in I (1).

Mass spectrum (ESI⁺): m/z=501 [M+H]⁺

(2) 3,5-dichloro-N-(1-pyrimidin-2-yl-2,3-dihydro-1H-indol-5-yl)-phenylsulphonamide

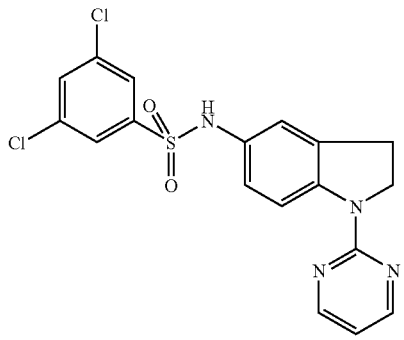 [SMILES: O=S(=O)(Nc1ccc2c(c1)CCN2c1ncccn1)c1cc(Cl)cc(Cl)c1]

The crude product is purified by chromatography on silica gel.
Mass spectrum (ESI$^+$): m/z=421 [M+H]$^+$

(3) 3,5-dichloro-N-[1-(1-methyl-1H-imidazol-2-yl)-2,3-dihydro-1H-indol-5-yl]-phenylsulphonamide

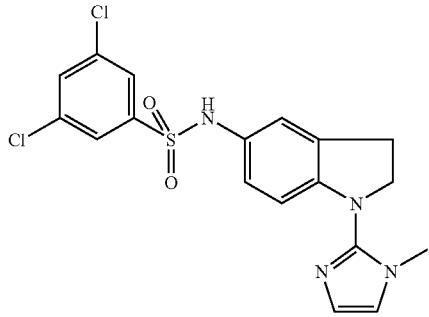 [SMILES: Cn1ccnc1N1CCc2cc(NS(=O)(=O)c3cc(Cl)cc(Cl)c3)ccc21]

Mass spectrum (ESI$^+$): m/z=423 [M+H]$^+$

Example III

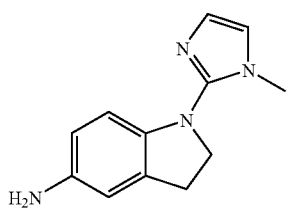

1-(1-methyl-1H-imidazol-2-yl)-2,3-dihydro-1H-indol-5-ylamine 170 mg 1-(1-methyl-1H-imidazol-2-yl)-5-nitro-2,3-dihydro-1H-indole are dissolved in 20 ml of tetrahydrofuran. To this are added 20 mg palladium on charcoal (10%) and the mixture is hydrogenated for 1 hour at ambient temperature. Then the catalyst is filtered off and the solvent is eliminated in vacuo. The crude product is extracted from diethyl ether.
Yield: 95 mg (64% of theory)
Mass spectrum (ESI$^+$): m/z=215 [M+H]$^+$ The following compounds are obtained analogously to Example III:

(1) 5-amino-1-(2,6-dichloro-phenyl)-1,3-dihydro-indol-2-one

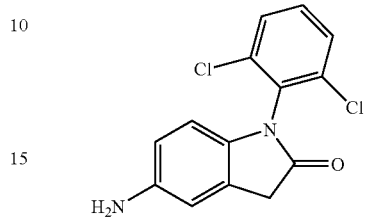

and 5-amino-1-(2-dichloro-phenyl)-1,3-dihydro-indol-2-one

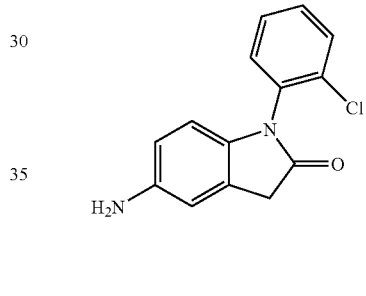

are obtained as a mixture by hydrogenating 1-(2,6-dichlorophenyl)-5-nitro-1,3-dihydro-indol-2-one. The hydrogenation is carried out in methanol/tetrahydrofuran 1:1. The crude product is further reacted directly in II (1).

(2) 1-pyrimidin-2-yl-2,3-dihydro-1H-indol-5-ylamine

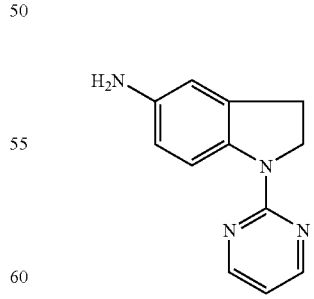

The reaction is carried out in dichloromethane/methanol 1:1. The crude product is further reacted directly in II (2).

Example IV

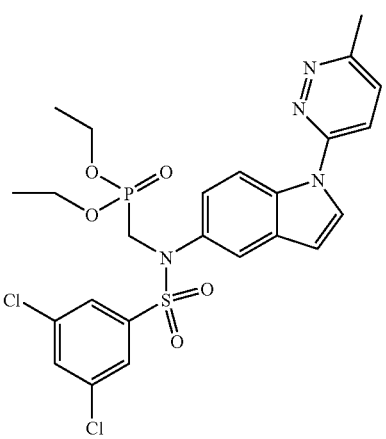 [SMILES: CCOP(=O)(CN(c1ccc2c(ccn2-c2ccc(C)nn2)c1)S(=O)(=O)c1cc(Cl)cc(Cl)c1)OCC]

Diethyl ({(3,5-dichloro-phenylsulphonyl)-[1-(6-methyl-pyridazin-3-yl)-1H-indol-5-yl]-amino}-methyl)-phosphonate 460 mg diethyl {[(3,5-dichloro-phenylsulphonyl)-(1H-indol-5-yl)-amino]-methyl}-phosphonate, 18 mg copper iodide and 596 mg potassium phosphate are placed in a flask. It is evacuated twice and filled with argon. Then 8 ml of toluene and 412 mg 3-iodo-6-methyl-pyridazine are added. After the addition of 30 μl N,N'-dimethyl-trans-cyclohexanediamine the mixture is heated to 90° C. for 12 hours. Then it is divided between water and ethyl acetate. The aqueous phase is extracted with ethyl acetate and the combined organic phases are dried on magnesium sulphate. The solvents are eliminated in vacuo and the residue is chromatographed on silica gel (cyclohexane/ethyl acetate 70:30 to 0:100).

Yield: 126 mg (23% of theory)
Mass spectrum (ESI$^+$): m/z=583 [M+H]$^+$

The following compounds are obtained analogously to Example IV:

(1) tert-butyl 3-(6-{5-[(3,5-dichloro-phenylsulphonyl)-(diethoxy-phosphorylmethyl)-amino]-indol-1-yl}-pyridazin-3-yl)-2-oxo-imidazolidine-1-carboxylate

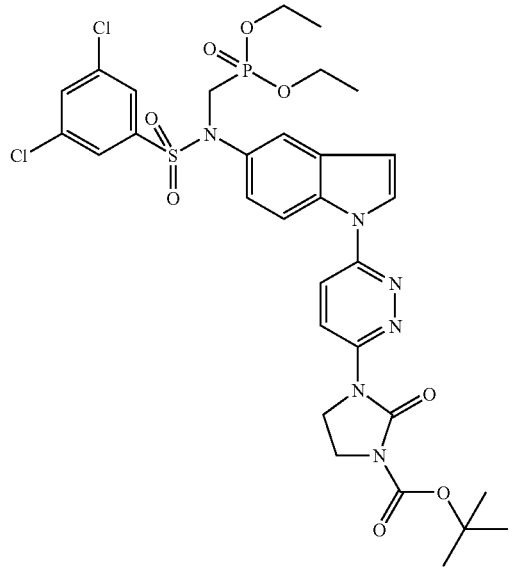 [SMILES: CCOP(=O)(CN(c1ccc2c(ccn2-c2ccc(N3CCN(C(=O)OC(C)(C)C)C3=O)nn2)c1)S(=O)(=O)c1cc(Cl)cc(Cl)c1)OCC]

Tert-butyl 3-(6-iodo-pyridazin-3-yl)-2-oxo-imidazolidine-1-carboxylate is used instead of 3-iodo-6-methyl-pyridazine.

Mass spectrum (ESI$^+$): m/z=753 [M+H]$^+$

Example V

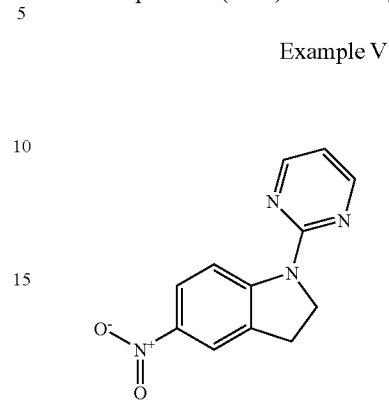

5-nitro-1-pyrimidin-2-yl-2,3-dihydro-1H-indole 300 mg 5-nitro-2,3-dihydro-1H-indole are dissolved in 4 ml N-methyl-pyrrolidine. 80 mg NaH (60% suspension in mineral oil) are added and the mixture is stirred for 15 minutes at ambient temperature. Then 380 mg of 2-bromopyrimidine are added and the mixture is then heated to 60° C. for 3 hours. It is then diluted with diethyl ether and washed with dilute citric acid solution and saturated sodium chloride solution. After drying with magnesium sulphate the solvents are eliminated in vacuo.

Yield: 410 mg (95% of theory)
Rf value: 0.61 (silica gel:ethyl acetate/petroleum ether 1:1)

Example VI

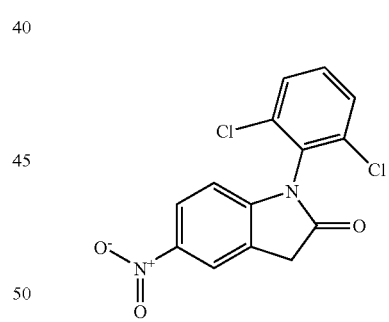

1-(2,6-dichloro-phenyl)-5-nitro-1,3-dihydro-indol-2-one 600 mg 1-(2,6-dichloro-phenyl)-1,3-dihydro-indol-2-one are dissolved in 5 ml concentrated sulphuric acid and cooled to 0° C. To this is added dropwise a solution of 160 μl concentrated nitric acid in 1 ml concentrated sulphuric acid. The mixture is stirred for 30 minutes and then added to 50 g ice. Then the mixture is stirred for 1 hour and the solid is suction filtered. After drying in vacuo the solid is chromatographed on silica gel (cyclohexane/ethyl acetate 70:30 to 20:80).

Yield: 310 mg (44% of theory)
Mass spectrum (ESI$^+$): m/z=323 [M+H]$^+$

Example VII

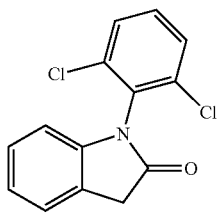 [SMILES: O=C1Cc2ccccc2N1c1c(Cl)cccc1Cl]

1-(2,6-dichloro-phenyl)-1,3-dihydro-indol-2-one 1.5 g sodium-[2-(2,6-dichloro-phenylamino)-phenyl]-acetate are dissolved in 6 ml of water, combined with 5.2 ml 1 N hydrochloric acid and the precipitated solid is suction filtered after stirring for 10 minutes. After drying in vacuo the solid is taken up in 6 ml of tetrahydrofuran, combined with 990 µl triethylamine and 1.17 g N-(3-dimethylaminopropyl)-N'-ethyl-carbodiimide-hydrochloride and stirred for 3 hours. Then it is divided between water and ethyl acetate, the aqueous phase is extracted twice with ethyl acetate and the combined organic phases are dried on magnesium sulphate. The solvents are eliminated in vacuo and the residue is chromatographed on silica gel (cyclohexane/ethyl acetate 70:30 to 20:80).
Yield: 610 mg (47% of theory)
Mass spectrum (ESI$^+$): m/z=278 [M+H]$^+$

Example VIII

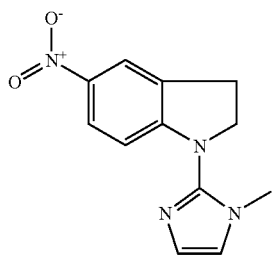 [SMILES: Cn1ccnc1N1CCc2cc([N+](=O)[O-])ccc21]

1-(1-methyl-1H-imidazol-2-yl)-5-nitro-2,3-dihydro-1H-indole 230 mg 1-(1H-imidazol-2-yl)-5-nitro-2,3-dihydro-1H-indole are dissolved in 6 ml dimethylformamide, combined with 200 mg potassium carbonate and 75 µl methyl iodide and stirred overnight at ambient temperature. The mixture is divided between ethyl acetate and 2 N hydrochloric acid and the aqueous phase is washed twice with dichloromethane. Then the pH of the aqueous phase is adjusted to 12 by the addition of 40% sodium hydroxide solution and it is extracted with dichloromethane. The organic phase is washed with saturated sodium chloride solution and dried on magnesium sulphate. The solvents are eliminated in vacuo and the residue is chromatographed on silica gel (dichloromethane/methanol 99:1 to 90:10).
Yield: 170 mg (70% of theory)
Mass spectrum (ESI$^+$): m/z=245 [M+H]$^+$

Example IX

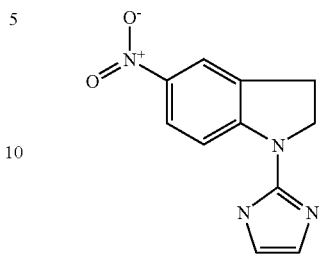

1-(1H-imidazol-2-yl)-5-nitro-2,3-dihydro-1H-indole 470 mg N-(2,2-diethoxy-ethyl)-5-nitro-2,3-dihydro-indole-1-carboxamidine are dissolved in 8 ml trifluoroacetic acid and the mixture is heated to 60° C. for 3 hours. Then the solvent is eliminated in vacuo and the residue is chromatographed on aluminium oxide (dichloromethane/methanol 99:1 to 70:30).
Yield: 230 mg (69% of theory)
Mass spectrum (ESI$^+$): m/z=229 [M−H]$^-$

Example X

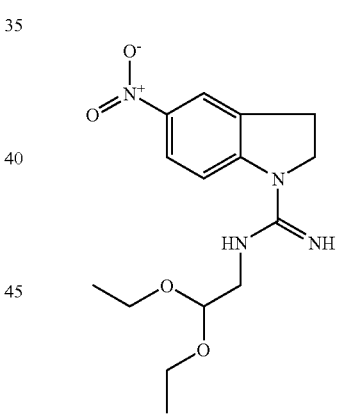

N-(2,2-diethoxy-ethyl)-5-nitro-2,3-dihydro-indole-1-carboxamidine 410 mg methyl 5-nitro-2,3-dihydro-indole-1-carboximidothionate are dissolved in 4 ml dimethylformamide, combined with 350 µl aminoacetaldehyde-diethylacetal and heated to 100° C. for 4 hours. The solvent is eliminated in vacuo and the residue is chromatographed on aluminium oxide (dichloromethane/methanol 99:1 to 95:5).
Yield: 330 mg (91% of theory)
Mass spectrum (ESI$^+$): m/z=323 [M+H]$^+$

Example XI

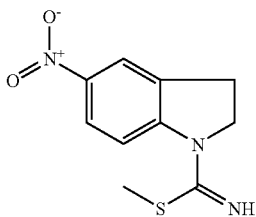 [SMILES: CSC(=N)N1CCc2cc([N+](=O)[O-])ccc21]

Methyl 5-nitro-2,3-dihydro-indole-1-carboximidothionate 1 g methyl 5-nitro-2,3-dihydro-indole-1-carboximidothionate*HI is suspended in 10 ml dichloromethane and combined with 2.75 ml 1 N sodium hydroxide solution. The mixture is stirred for 1 hour at ambient temperature, then dried with magnesium sulphate and the solvent is eliminated in vacuo.

Yield: 640 mg (99% of theory)
Mass spectrum (ESI$^+$): m/z=238 [M+H]$^+$

Example XII

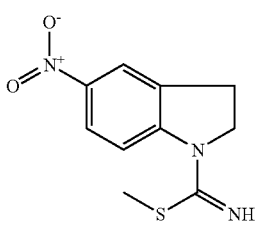 [SMILES: CSC(=N)N1CCc2cc([N+](=O)[O-])ccc21]

Methyl 5-nitro-2,3-dihydro-indole-1-carboximidothionate*HI 3.5 g 5-nitro-2,3-dihydro-indole-1-carbothionic acid amide are dissolved in 50 ml dimethylformamide, combined with 1.2 ml methyl iodide and stirred overnight at ambient temperature. The solvent is eliminated in vacuo and the residue is extracted from diethyl ether.

Yield: 4.85 g (85% of theory)
Mass spectrum (ESI$^+$): m/z=238 [M+H]$^+$

Example XIII

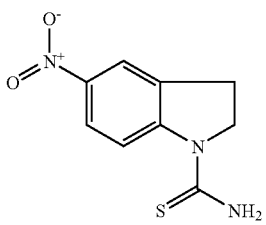

5-nitro-2,3-dihydro-indole-1-carbothionic acid-amide 5 g 5-nitro-2,3-dihydro-1H-indole are dissolved in 100 ml dichloromethane, cooled to 0° C., combined with 298 N,N-diisopropyl-N-ethyl-amine and 2.4 ml of thiophosgene and stirred for 1.5 hours. The mixture is then diluted with 300 ml of tetrahydrofuran and ammonia is then piped into the solution for 1 hour. It is then left to come up to ambient temperature and stirred overnight. The solvents are eliminated in vacuo, the residue is extracted from dilute hydrochloric acid and dried.

Yield: 6.35 g (96% of theory)
Mass spectrum (ESI$^+$): m/z=224 [M+H]$^+$

Example XIV

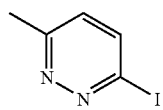

3-iodo-6-methyl-pyridazine 2.5 g 3-chloro-6-methyl-pyridazine are dissolved in 10 ml of 57% hydrogen iodide solution and heated for 2 hours to 120° C. Then the mixture is cooled to 0° C. and carefully neutralised with 1 N sodium hydroxide solution. The aqueous phase is extracted twice with ethyl acetate and the combined organic phases are washed twice with water and once with saturated sodium chloride solution. After drying with magnesium sulphate the solvent is eliminated in vacuo.

Yield: 3.6 g (84% of theory)
Mass spectrum (ESI$^+$): m/z=221 [M+H]$^+$

The following compounds are obtained analogously to Example XIV:

(1) 3,6-diiodo-pyridazine

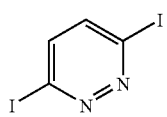

After the reaction has ended the mixture is added to ice and then made alkaline by the addition of 40% sodium hydroxide solution. The precipitated solid is suction filtered, dissolved in dichloromethane and the organic phase is washed with saturated sodium thiosulphate solution. After drying with magnesium sulphate the solvent is eliminated in vacuo and the residue is extracted from diethyl ether.

Mass spectrum (ESI$^+$): m/z=333 [M+H]$^+$

Example XV

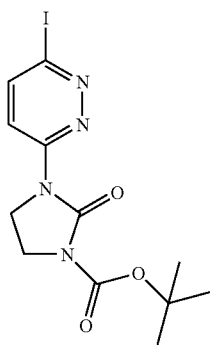 [SMILES: CC(C)(C)OC(=O)N1CCN(c2ccc(I)nn2)C1=O]

tert-butyl 3-(6-iodo-pyridazin-3-yl)-2-oxo-imidazolidine-1-carboxylate 385 mg tert. butyl [2-(6-iodo-pyridazin-3-ylamino)-ethyl]-carbamate are dissolved in 10 ml dichloromethane, combined with 360 μl N,N-diisopropyl-N-ethyl-amine and 560 μl of a 20% solution of phosgene in toluene are added dropwise thereto. After stirring overnight the mixture is diluted with ethyl acetate and washed with semisaturated sodium chloride solution. After drying with magnesium sulphate the solvents are eliminated in vacuo and the residue is extracted from diethyl ether.
Yield: 270 mg (65% of theory)
Mass spectrum (ESI$^+$): m/z=391 [M+H]$^+$

Example XVI

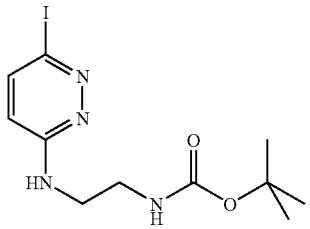 [SMILES: CC(C)(C)OC(=O)NCCNc1ccc(I)nn1]

tert. butyl [2-(6-iodo-pyridazin-3-ylamino)-ethyl]-carbamate 800 mg N*1*-(6-iodo-pyridazin-3-yl)-ethane-1,2-diamine are dissolved in 20 ml of tetrahydrofuran, combined with 700 mg di-tert.-butyl-dicarbonate and heated for 3 h to 60° C. The solvent is then eliminated in vacuo and the residue is extracted from diethyl ether.
Yield: 390 mg (35% of theory)
Mass spectrum (ESI$^+$): m/z=365 [M+H]$^+$

Example XVII

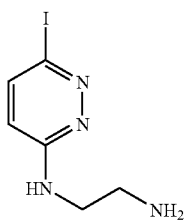

N*1*-(6-iodo-pyridazin-3-yl)-ethane-1,2-diamine 1 g 3,6-diiodopyridazine is dissolved in 6 ml dioxane, combined with 440 mg potassium carbonate and 220 μl of 1,2-diaminoethane and heated for 12 hours to 120° C. The mixture is diluted with dichloromethane, the insoluble constituents are filtered off and the solvents are eliminated in vacuo.
Yield: 800 mg (101% of theory)
Rf value: 0.31 (aluminium oxide:dichloromethane/methanol 5:1)

Example XVIII

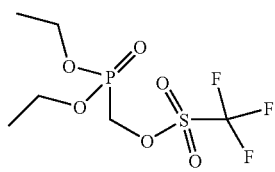 [SMILES: CCOP(=O)(COS(=O)(=O)C(F)(F)F)OCC]

Diethoxy-phosphorylmethyl trifluoro-methanesulphonate 5.01 ml diethyl-(hydroxyethyl)-phosphonate are dissolved in 50 ml dichloromethane, combined with 4.42 ml of 2,6-lutidine and cooled to −50° C. Then a solution of 6 ml trifluoromethanesulphonic acid anhydride in 10 ml dichloromethane is slowly added dropwise. The mixture is allowed to come up to 0° C. within 1.5 hours and then diluted with 300 ml of cold diethyl ether. The precipitated solids are filtered off and the filtrate is washed twice with ice water, once with 1 N hydrochloric acid and once with saturated sodium chloride solution. After drying with sodium sulphate the solvents are eliminated in vacuo.
Yield: 8.2 g (89% of theory)
Mass spectrum (ESI$^+$): m/z=301 [M+H]$^+$

PREPARATION OF THE END COMPOUNDS

Example 1

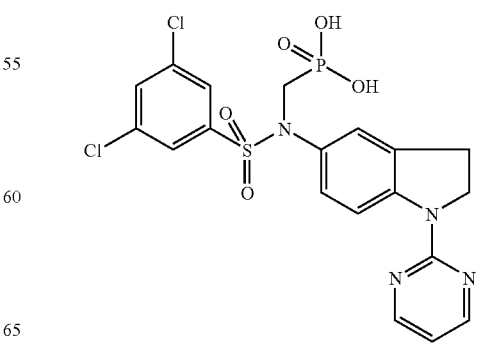

{[(3,5-dichloro-phenylsulphonyl)-(1-pyrimidin-2-yl-2,3-dihydro-1H-indol-5-yl)-amino]-methyl}-phosphonic acid 70 mg diethyl {[(3,5-dichloro-phenylsulphonyl)-(1-pyrimidin-2-yl-2,3-dihydro-1H-indol-5-yl)-amino]-methyl}-phosphonate are dissolved in 3 ml dichloromethane. Under argon 200 μl trimethylsilylbromide are added thereto and the mixture is refluxed for 2 hours. After cooling to ambient temperature 1 ml of methanol is added and the mixture is stirred for a further 1 hour. Then the solvents are eliminated in vacuo. The residue is taken up in 3 ml of methanol, stirred for 10 minutes and the solvent is eliminated in vacuo. The residue thus obtained is extracted from dichloromethane with 1% methanol. The solid is suction filtered and dried.

Yield: 40 mg (63% of theory)
Mass spectrum (ESI$^+$): m/z=513 [M−H]$^-$

The following compounds are obtained analogously to Example 1:

(1) {[[1-(2-chloro-phenyl)-2-oxo-2,3-dihydro-1H-indol-5-yl]-(3,5-dichloro-phenylsulphonyl)-amino]-methyl}-phosphonic acid

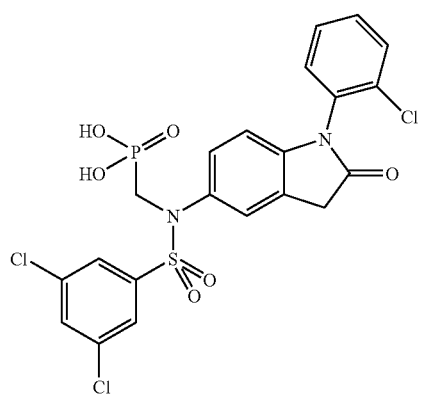 [SMILES: O=C1Cc2cc(N(CP(=O)(O)O)S(=O)(=O)c3cc(Cl)cc(Cl)c3)ccc2N1c1ccccc1Cl]

The product is extracted from diethyl ether/cyclohexane.
Mass spectrum (ESI$^+$): m/z=559 [M−H]$^-$ (2) ({(3,5-dichloro-phenylsulphonyl)-[1-(2,6-dichloro-phenyl)-2-oxo-2,3-dihydro-1H-indol-5-yl]-amino}-methyl)-phosphonic acid

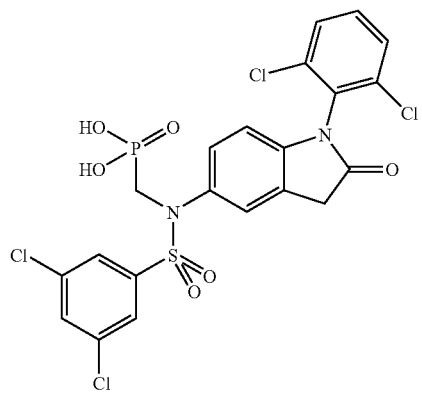 [SMILES: O=C1Cc2cc(N(CP(=O)(O)O)S(=O)(=O)c3cc(Cl)cc(Cl)c3)ccc2N1c1c(Cl)cccc1Cl]

The product is extracted from diethyl ether/cyclohexane.
Mass spectrum (ESI$^+$): m/z=593 [M−H]$^-$ (3) ({(3,5-dichloro-phenylsulphonyl)-[1-(1-methyl-1H-imidazol-2-yl)-2,3-dihydro-1H-indol-5-yl]-amino}-methyl)-phosphonic acid

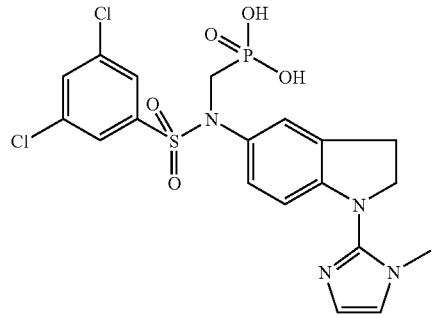 [SMILES: Cn1ccnc1N1CCc2cc(N(CP(=O)(O)O)S(=O)(=O)c3cc(Cl)cc(Cl)c3)ccc21]

The product is extracted from diisopropylether.
Mass spectrum (ESI$^+$): m/z=515 [M−H]$^-$ (4) ({(3,5-dichloro-phenylsulphonyl)-[1-(6-methyl-pyridazin-3-yl)-1H-indol-5-yl]-amino}-methyl)-phosphonic acid

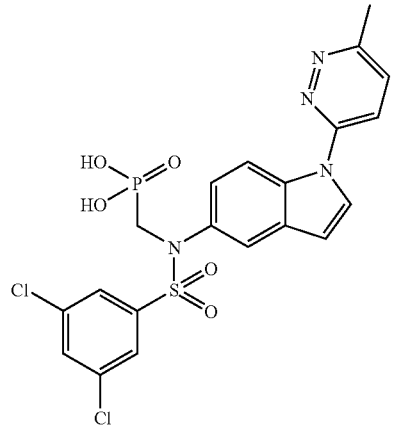 [SMILES: Cc1ccc(-n2ccc3cc(N(CP(=O)(O)O)S(=O)(=O)c4cc(Cl)cc(Cl)c4)ccc32)nn1]

The product is extracted from diethyl ether.
Mass spectrum (ESI$^+$): m/z=527 [M+H]$^+$ (5) [((3,5-dichloro-phenylsulphonyl)-{1-[6-(2-oxo-imidazolidin-1-yl)-pyridazin-3-yl]-1H-indol-5-yl}-amino)-methyl]-phosphonic acid

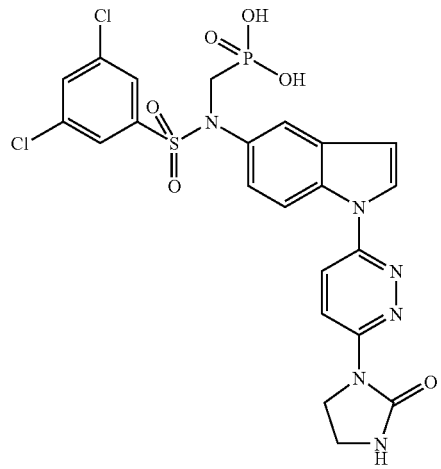 [SMILES: O=C1NCCN1c1ccc(-n2ccc3cc(N(CP(=O)(O)O)S(=O)(=O)c4cc(Cl)cc(Cl)c4)ccc32)nn1]

The product is extracted from diethyl ether.
Mass spectrum (ESI$^+$): m/z=597 [M+H]$^+$ The following compounds are obtained analogously to the foregoing Examples and other methods known from the literature:

| No. | Name | Structural formula |
|---|---|---|
| (1) | {[(3,5-dichloro-phenylsulphonyl)-(1-pyrazin-2-yl-1H-indol-5-yl)-amino]-methyl}-phosphonic acid | |
| (2) | ({(3,5-dichloro-phenylsulphonyl)-[1-(3-methylcarbamoyl-phenyl)-1H-indol-5-yl]-amino}-methyl)-phosphonic acid | |
| (3) | ({(3,5-dichloro-phenylsulphonyl)-[1-(4-methyl-6-piperazin-1-yl-pyridazin-3-yl)-1H-indol-5-yl]-amino}-methyl)-phosphonic acid | |

-continued

| No. | Name | Structural formula |
|---|---|---|
| (4) | [((3,5-dichloro-phenylsulphonyl)-{1-[6-(2-dimethylamino-ethylamino)-pyridazin-3-yl]-1H-indol-5-yl}-amino)-methyl]-phosphonic acid | 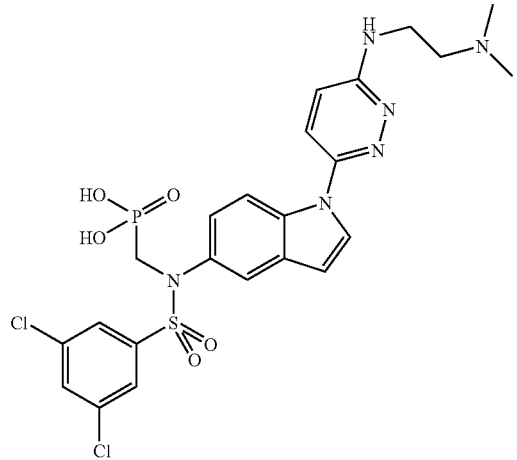 |
| (5) | {[{1-[6-(2-dimethylamino-ethylamino)-pyridazin-3-yl]-1H-indol-5-yl}-(3,5-dimethyl-phenylsulphonyl)-amino]-methyl}-phosphonic acid | 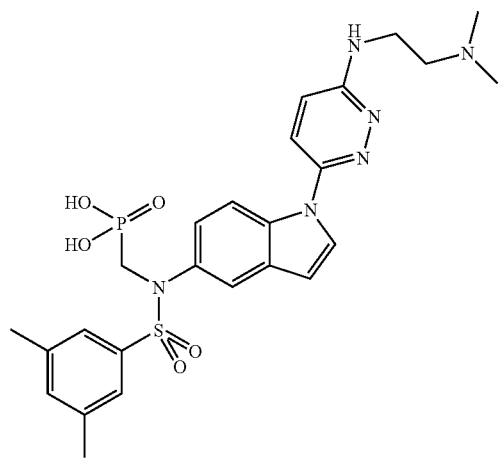 |
| (6) | [((3-bromo-5-methyl-phenylsulphonyl)-{1-[6-(2-dimethylamino-ethylamino)-pyridazin-3-yl]-1H-indol-5-yl}-amino)-methyl]-phosphonic acid | 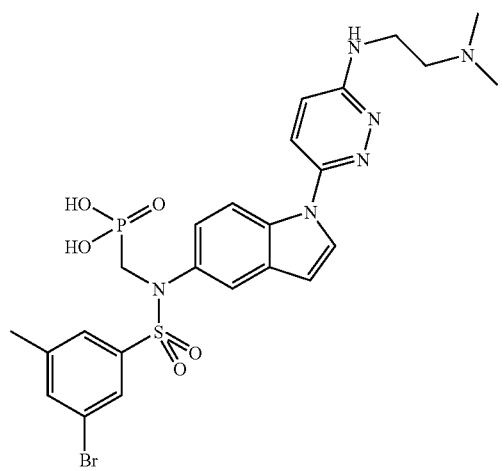 |

-continued

| No. | Name | Structural formula |
|---|---|---|
| (7) | ({(3,5-dichloro-phenylsulphonyl)-[1-(2-methylamino-pyrimidin-4-yl)-1H-indol-5-yl]-amino}-methyl)-phosphonic acid | |
| (8) | {[[1-(5-amino-pyridin-2-yl)-1H-indol-5-yl]-(3,5-dichloro-phenylsulphonyl)-amino]-methyl}-phosphonic acid | |
| (9) | {[[1-(6-[1.4]diazepan-1-yl-pyridazin-3-yl)-1H-indol-5-yl]-(3,5-dichloro-phenylsulphonyl)-amino]-methyl}-phosphonic acid | |

| No. | Name | Structural formula |
|---|---|---|
| (10) | {[[1-(6-cyclopropylamino-pyridazin-3-yl)-1H-indol-5-yl]-(3,5-dichloro-phenylsulphonyl)-amino]-methyl}-phosphonic acid | 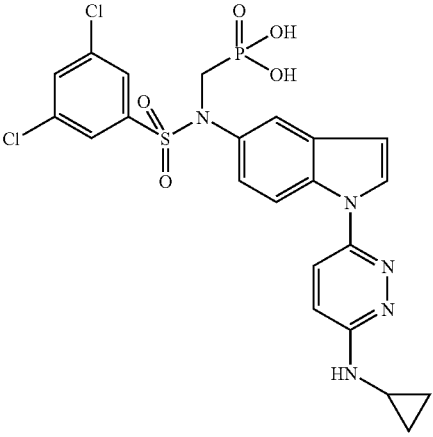 [SMILES: O=P(O)(O)CN(c1ccc2c(ccn2-c2ccc(NC3CC3)nn2)c1)S(=O)(=O)c1cc(Cl)cc(Cl)c1] |
| (11) | [((3,5-dichloro-phenylsulphonyl)-{1-[6-(2-dimethylamino-ethylamino)-pyridazin-3-yl]-3-methyl-1H-indol-5-yl}-amino)-methyl]-phosphonic acid | 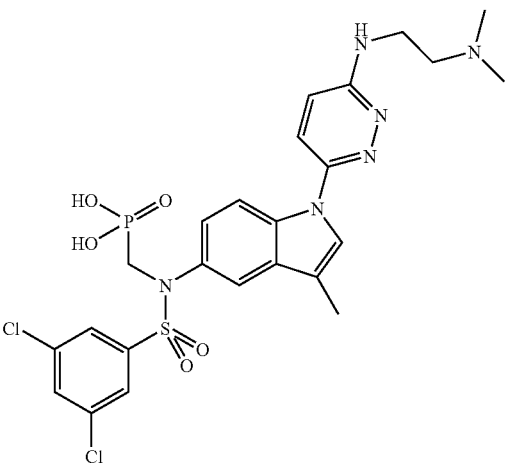 [SMILES: Cc1cn(-c2ccc(NCCN(C)C)nn2)c2ccc(N(CP(=O)(O)O)S(=O)(=O)c3cc(Cl)cc(Cl)c3)cc12] |
| (12) | [((3,5-dichloro-phenylsulphonyl)-{1-[6-(2-methylamino-ethylamino)-pyridazin-3-yl]-1H-indol-5-yl}-amino)-methyl]-phosphonic acid | 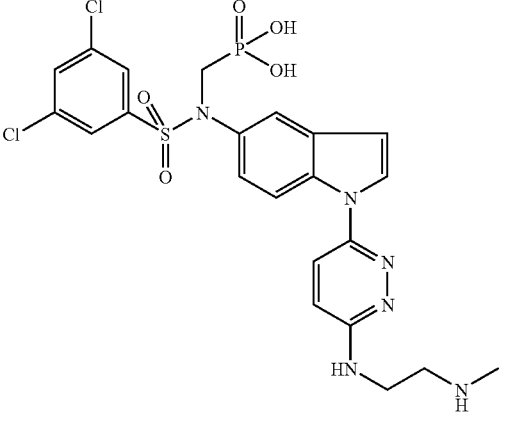 [SMILES: CNCCNc1ccc(-n2ccc3cc(N(CP(=O)(O)O)S(=O)(=O)c4cc(Cl)cc(Cl)c4)ccc32)nn1] |

| No. | Name | Structural formula |
|---|---|---|
| (13) | {[{1-[6-(2-amino-2-methyl-propylamino)-pyridazin-3-yl]-1H-indol-5-yl}-(3,5-dichloro-phenylsulphonyl)-amino]-methyl}-phosphonic acid | |
| (14) | ({(3,5-dichloro-phenylsulphonyl)-[1-(6-morpholin-4-yl-pyridazin-3-yl)-1H-indol-5-yl]-amino}-methyl)-phosphonic acid | |
| (15) | ({(3,5-dichloro-phenylsulphonyl)-[1-(4,6-dimethoxy-[1.3.5]triazin-2-yl)-2,3-dihydro-1H-indol-5-yl]-amino}-methyl)-phosphonic acid | |

-continued

| No. | Name | Structural formula |
|---|---|---|
| (16) | [((3,5-dichloro-phenylsulphonyl)-{1-[6-(2-hydroxy-ethylamino)-pyridazin-3-yl]-1H-indol-5-yl}-amino)-methyl]-phosphonic acid | |
| (17) | [((3,5-dichloro-phenylsulphonyl)-{1-[5-(3-oxo-morpholin-4-yl)-pyrazin-2-yl]-1H-indol-5-yl}-amino)-methyl]-phosphonic acid | |
| (18) | ((3,5-dichloro-phenylsulphonyl)-{1-[5-(tetrahydro-pyran-4-yloxy)-pyrazin-2-yl]-1H-indol-5-yl}-amino)-methyl]-phosphonic acid | |

| No. | Name | Structural formula |
|---|---|---|
| (19) | [((3,5-dichloro-phenylsulphonyl)-{1-[5-(tetrahydro-furan-3-yloxy)-pyrazin-2-yl]-1H-indol-5-yl}-amino)-methyl]-phosphonic acid | 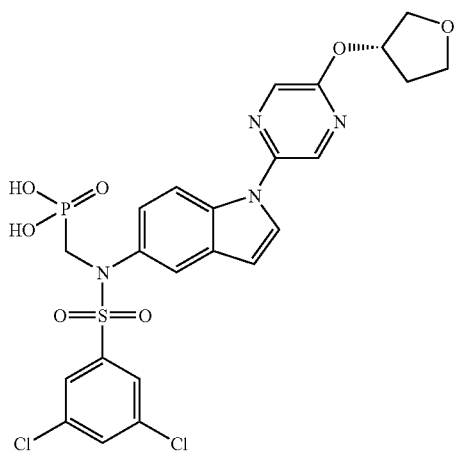 [SMILES: O=P(O)(O)CN(c1ccc2c(ccn2-c2cnc(O[C@H]3CCOC3)cn2)c1)S(=O)(=O)c1cc(Cl)cc(Cl)c1] |
| (20) | [((3,5-dichloro-phenylsulphonyl)-{1-[5-(tetrahydro-pyran-4-ylamino)-pyrazin-2-yl]-1H-indol-5-yl}-amino)-methyl]-phosphonic acid | 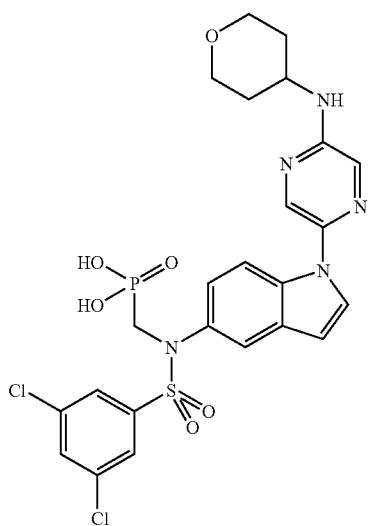 [SMILES: O=P(O)(O)CN(c1ccc2c(ccn2-c2cnc(NC3CCOCC3)cn2)c1)S(=O)(=O)c1cc(Cl)cc(Cl)c1] |
| (21) | ({(3,5-dichloro-phenylsulphonyl)-[1-(5-trifluoromethyl-pyridazin-3-yl)-1H-indol-5-yl]-amino}-methyl)-phosphonic acid | 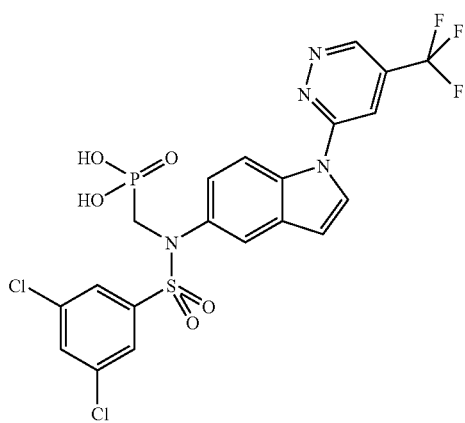 [SMILES: O=P(O)(O)CN(c1ccc2c(ccn2-c2cc(C(F)(F)F)cnn2)c1)S(=O)(=O)c1cc(Cl)cc(Cl)c1] |

| No. | Name | Structural formula |
|---|---|---|
| (22) | [((3,5-dichloro-phenylsulphonyl)-{1-[6-(2-dimethylamino-ethoxy)-pyridazin-3-yl]-1H-indol-5-yl}-amino)-methyl]-phosphonic acid | 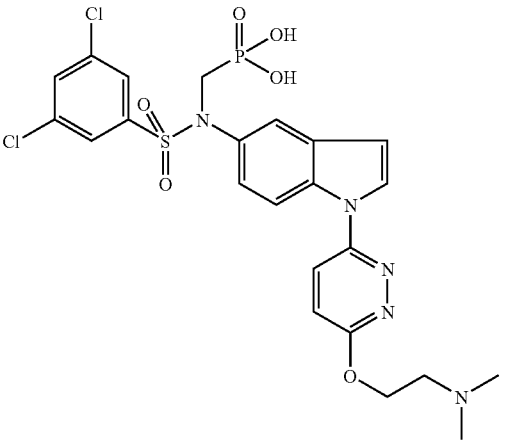 [SMILES: CN(C)CCOc1ccc(-n2ccc3cc(N(CP(=O)(O)O)S(=O)(=O)c4cc(Cl)cc(Cl)c4)ccc32)nn1] |
| (23) | ({(3,5-dichloro-phenylsulphonyl)-[1-(1,3-dimethyl-2,4-dioxo-1,2,3,4-tetrahydro-pyrimidin-5-yl)-1H-indol-5-yl]-amino}-methyl)-phosphonic acid | 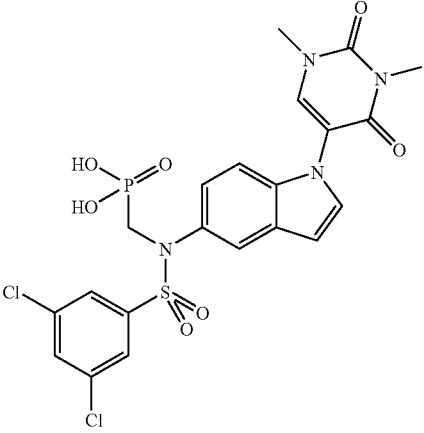 [SMILES: Cn1cc(-n2ccc3cc(N(CP(=O)(O)O)S(=O)(=O)c4cc(Cl)cc(Cl)c4)ccc32)c(=O)n(C)c1=O] |
| (24) | ({(3,5-dichloro-phenylsulphonyl)-[1-(6-oxo-1,6-dihydro-pyridazin-3-yl)-1H-indol-5-yl]-amino}-methyl)-phosphonic acid | 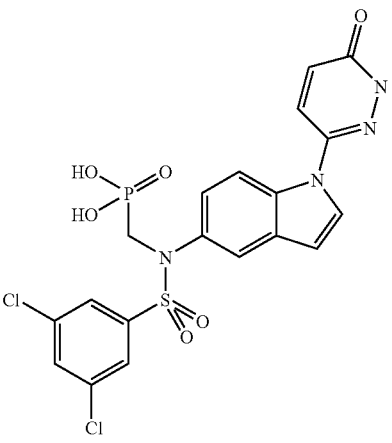 [SMILES: O=c1ccc(-n2ccc3cc(N(CP(=O)(O)O)S(=O)(=O)c4cc(Cl)cc(Cl)c4)ccc32)n[nH]1] |

| No. | Name | Structural formula |
|---|---|---|
| (25) | ({(3,5-dichloro-phenylsulphonyl)-[1-(6-methylsulphanyl-pyridazin-3-yl)-1H-indol-5-yl]-amino}-methyl)-phosphonic acid | |
| (26) | ({(3,5-dichloro-phenylsulphonyl)-[1-(4-methylcarbamoyl-pyridin-2-yl)-1H-indol-5-yl]-amino}-methyl)-phosphonic acid | |
| (27) | ({(3,5-dichloro-phenylsulphonyl)-[3-methyl-1-(6-methyl-pyridazin-3-yl)-1H-indol-5-yl]-amino}-methyl)-phosphonic acid | |

| No. | Name | Structural formula |
|---|---|---|
| (28) | ({(3,5-dichloro-phenylsulphonyl)-[1-(6-thiomorpholin-4-yl-pyridazin-3-yl)-1H-indol-5-yl]-amino}-methyl)-phosphonic acid | |
| (29) | [((3,5-dichloro-phenylsulphonyl)-{1-[6-(1,1-dioxo-1lambda*6*-thiomorpholin-4-yl)-pyridazin-3-yl]-1H-indol-5-yl}-amino)-methyl]-phosphonic acid | |
| (30) | [((3,5-dichloro-phenylsulphonyl)-{1-[6-(2,3-dihydroxy-propoxy)-pyridazin-3-yl]-1H-indol-5-yl}-amino)-methyl]-phosphonic acid | |

| No. | Name | Structural formula |
|---|---|---|
| (31) | ({(3,5-dichloro-phenylsulphonyl)-[1-(4-methanesulphinyl-pyridin-2-yl)-1H-indol-5-yl]-amino}-methyl)-phosphonic acid | |
| (32) | [((3,5-dichloro-phenylsulphonyl)-{1-[6-(1-oxo-1lambda*4*-thiomorpholin-4-yl)-pyridazin-3-yl]-1H-indol-5-yl}-amino)-methyl]-phosphonic acid | |
| (33) | ({(3,5-dichloro-phenylsulphonyl)-[3-ethyl-1-(6-methyl-pyridazin-3-yl)-1H-indol-5-yl]-amino}-methyl)-phosphonic acid | |

-continued

| No. | Name | Structural formula |
|---|---|---|
| (34) | ({(3,5-dichloro-phenylsulphonyl)-[1-(4-thiazol-2-yl-pyridin-2-yl)-1H-indol-5-yl]-amino}-methyl)-phosphonic acid | |
| (35) | {[[1-(4-cyclopropylcarbamoyl-pyridin-2-yl)-1H-indol-5-yl]-(3,5-dichloro-phenylsulphonyl)-amino]-methyl}-phosphonic acid | |
| (36) | methyl 2-{5-[(3,5-dichloro-phenylsulphonyl)-phosphonomethyl-amino]-indol-1-yl}-isonicotinate | |
| (37) | ({(3,5-dichloro-phenylsulphonyl)-[1-(4-ethanesulphinyl-pyridin-2-yl)-1H-indol-5-yl]-amino}-methyl)-phosphonic acid | |

-continued
| No. | Name | Structural formula |
|---|---|---|
| (38) | ({(3,5-dichloro-phenylsulphonyl)-[1-(4-oxazol-2-yl-pyridin-2-yl)-1H-indol-5-yl]-amino}-methyl)-phosphonic acid | 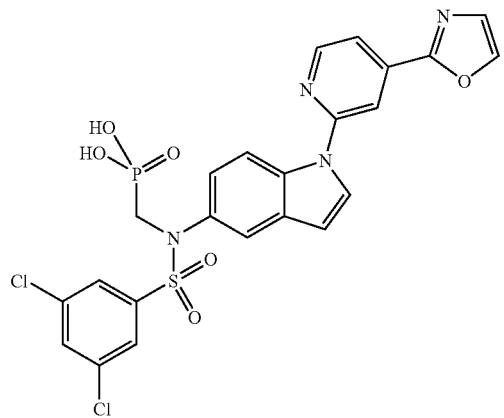 [SMILES: O=P(O)(O)CN(c1ccc2c(ccn2-c2cc(-c3ncco3)ccn2)c1)S(=O)(=O)c1cc(Cl)cc(Cl)c1] |
| (39) | {[[1-(4-acetyl-pyridin-2-yl)-1H-indol-5-yl]-(3,5-dichloro-phenylsulphonyl)-amino]-methyl}-phosphonic acid | 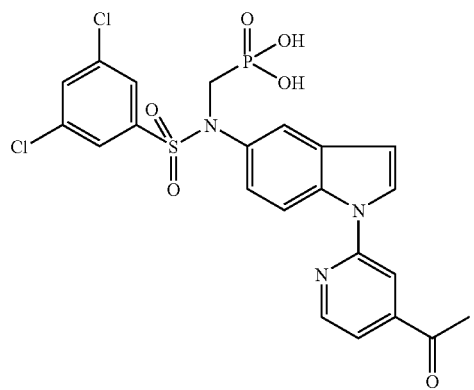 [SMILES: CC(=O)c1ccnc(-n2ccc3cc(N(CP(=O)(O)O)S(=O)(=O)c4cc(Cl)cc(Cl)c4)ccc32)c1] |
| (40) | ({(3,5-dichloro-phenylsulphonyl)-[1-(4-propionyl-pyridin-2-yl)-1H-indol-5-yl]-amino}-methyl)-phosphonic acid | 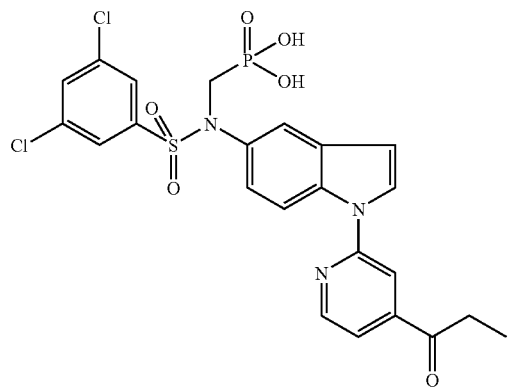 [SMILES: CCC(=O)c1ccnc(-n2ccc3cc(N(CP(=O)(O)O)S(=O)(=O)c4cc(Cl)cc(Cl)c4)ccc32)c1] |

| No. | Name | Structural formula |
|---|---|---|
| (41) | ({(3,5-dichloro-phenylsulphonyl)-[1-(6-dimethylcarbamoyl-pyridazin-3-yl)-1H-indol-5-yl]-amino}-methyl)-phosphonic acid | |
| (42) | {[[1-(4-cyclopropylcarbamoyl-pyridin-2-yl)-3-methyl-1H-indol-5-yl]-(3,5-dichloro-phenylsulphonyl)-amino]-methyl}-phosphonic acid | |
| (43) | [((3,5-dichloro-phenylsulphonyl)-{1-[4-(1-methyl-1H-imidazol-2-yl)-pyridin-2-yl]-1H-indol-5-yl}-amino)-methyl]-phosphonic acid | |

| No. | Name | Structural formula |
|---|---|---|
| (44) | {[[1-(4-aminomethyl-pyridin-2-yl)-1H-indol-5-yl]-(3,5-dichloro-phenylsulphonyl)-amino]-methyl}-phosphonic acid | 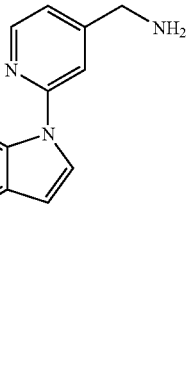 |
| (45) | ({(3,5-dichloro-phenylsulphonyl)-[1-(1-methyl-1H-pyrazol-4-yl)-1H-indol-5-yl]-amino}-methyl)-phosphonic acid | 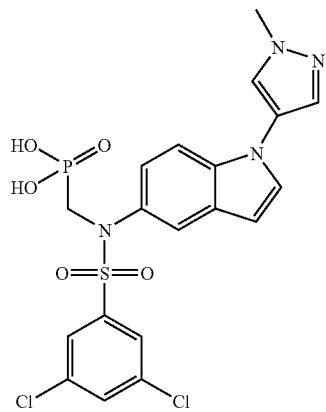 [SMILES: Cn1cc(-n2ccc3cc(N(CP(=O)(O)O)S(=O)(=O)c4cc(Cl)cc(Cl)c4)ccc32)cn1] |
| (46) | ({(3,5-dichloro-phenylsulphonyl)-[1-(1-methyl-1H-imidazol-4-yl)-1H-indol-5-yl]-amino}-methyl)-phosphonic acid | 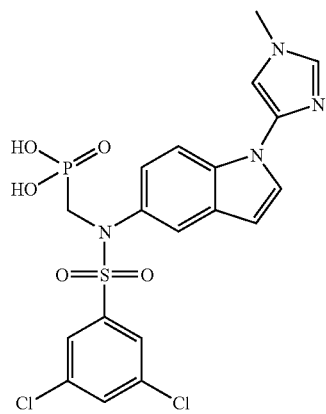 [SMILES: Cn1cnc(-n2ccc3cc(N(CP(=O)(O)O)S(=O)(=O)c4cc(Cl)cc(Cl)c4)ccc32)c1] |

| No. | Name | Structural formula |
|---|---|---|
| (47) | ({(3,5-dichloro-phenylsulphonyl)-[1-(6-trifluoromethyl-pyrimidin-4-yl)-1H-indol-5-yl]-amino}-methyl)-phosphonic acid | 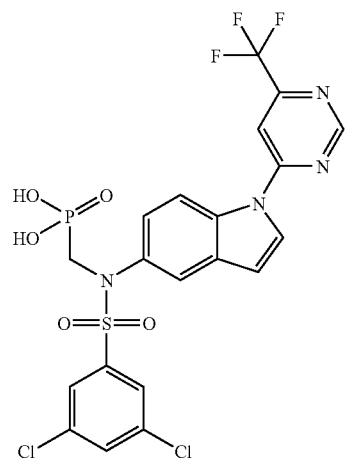 [SMILES: O=P(O)(O)CN(c1ccc2c(ccn2-c2cc(C(F)(F)F)ncn2)c1)S(=O)(=O)c1cc(Cl)cc(Cl)c1] |
| (48) | {[(3,5-dichloro-phenylsulphonyl)-(1-thiazol-2-yl-1H-indol-5-yl)-amino]-methyl}-phosphonic acid | 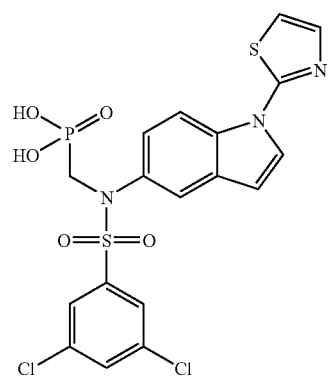 [SMILES: O=P(O)(O)CN(c1ccc2c(ccn2-c2nccs2)c1)S(=O)(=O)c1cc(Cl)cc(Cl)c1] |
| (49) | ({(3,5-dichloro-phenylsulphonyl)-[1-(5-methyl-[1.3.4]thiadiazol-2-yl)-1H-indol-5-yl]-amino}-methyl)-phosphonic acid | 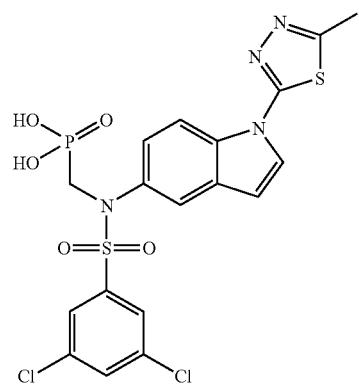 [SMILES: Cc1nnc(-n2ccc3cc(N(CP(=O)(O)O)S(=O)(=O)c4cc(Cl)cc(Cl)c4)ccc32)s1] |

-continued
| No. | Name | Structural formula |
|---|---|---|
| (50) | ({(2,6-dimethyl-pyridine-4-sulphonyl)-[1-(6-methyl-pyridazin-3-yl)-1H-indol-5-yl]-amino}-methyl)-phosphonic acid | 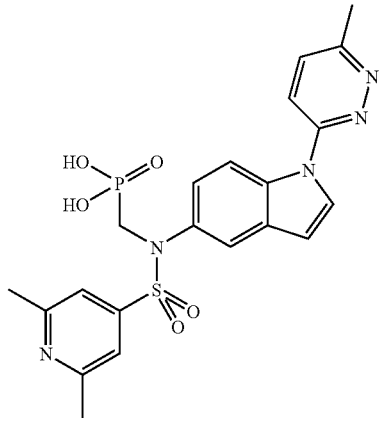 [SMILES: Cc1ccc(-n2ccc3cc(N(CP(=O)(O)O)S(=O)(=O)c4cc(C)nc(C)c4)ccc32)nn1] |
| (51) | {[{1-[5-(2-acetylamino-ethylamino)-pyrazin-2-yl]-1H-indol-5-yl}-(3,5-dichloro-phenylsulphonyl)-amino]-methyl}-phosphonic acid | 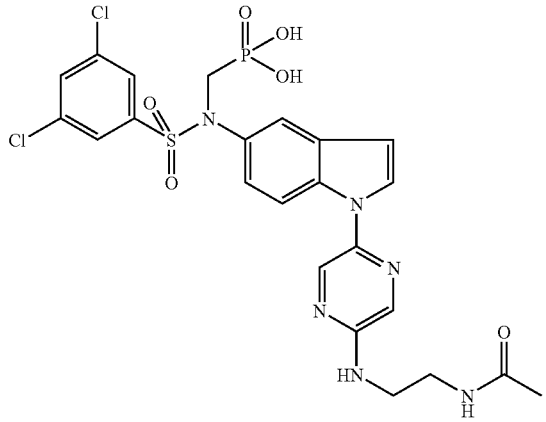 [SMILES: CC(=O)NCCNc1cnc(-n2ccc3cc(N(CP(=O)(O)O)S(=O)(=O)c4cc(Cl)cc(Cl)c4)ccc32)cn1] |
| (52) | {[[1-(4-acetylamino-pyridin-2-yl)-1H-indol-5-yl]-(3,5-dichloro-phenylsulphonyl)-amino]-methyl}-phosphonic acid | 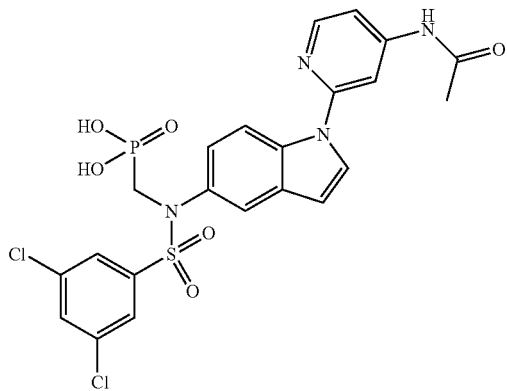 [SMILES: CC(=O)Nc1ccnc(-n2ccc3cc(N(CP(=O)(O)O)S(=O)(=O)c4cc(Cl)cc(Cl)c4)ccc32)c1] |

| No. | Name | Structural formula |
|---|---|---|
| (53) | {[{1-[6-(4-acetyl-piperazin-1-yl)-pyridazin-3-yl]-1H-indol-5-yl}-(3,5-dichloro-phenylsulphonyl)-amino]-methyl}-phosphonic acid | |
| (54) | ({(3,5-dichloro-phenylsulphonyl)-[1-(5-hydroxymethyl-pyridin-2-yl)-1H-indol-5-yl]-amino}-methyl)-phosphonic acid | |
| (55) | [((3,5-dichloro-phenylsulphonyl)-{1-[6-(3-hydroxy-propyl)-pyridazin-3-yl]-1H-indol-5-yl}-amino)-methyl]-phosphonic acid | |

| No. | Name | Structural formula |
|---|---|---|
| (56) | ({(3,5-dichloro-phenylsulphonyl)-[1-(2,4-dioxo-1,2,3,4-tetrahydro-pyrimidin-5-yl)-1H-indol-5-yl]-amino}-methyl)-phosphonic acid | |
| (57) | ({(3,5-dichloro-phenylsulphonyl)-[1-(2,6-dioxo-1,2,3,6-tetrahydro-pyrimidin-4-yl)-1H-indol-5-yl]-amino}-methyl)-phosphonic acid | |
| (58) | [((3,5-dichloro-phenylsulphonyl)-{1-[5-(2-methanesulphonylamino-ethylamino)-pyrazin-2-yl]-1H-indol-5-yl}-amino)-methyl]-phosphonic acid | |

| No. | Name | Structural formula |
|---|---|---|
| (59) | [((3,5-dichloro-phenylsulphonyl)-{1-[6-(4-methanesulphonyl-piperazin-1-yl)-pyridazin-3-yl]-1H-indol-5-yl}-amino)-methyl]-phosphonic acid | 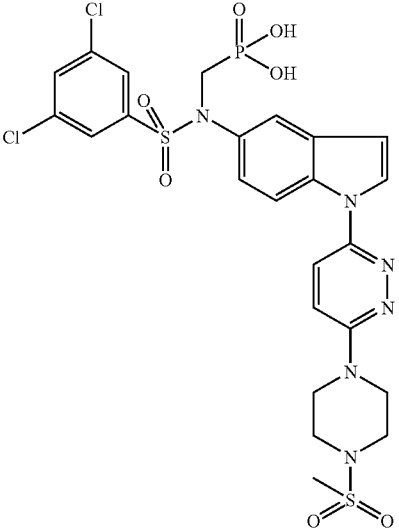 [SMILES: CS(=O)(=O)N1CCN(c2ccc(-n3ccc4cc(N(CP(=O)(O)O)S(=O)(=O)c5cc(Cl)cc(Cl)c5)ccc43)nn2)CC1] |
| (60) | {[[1-(5-cyano-pyridin-2-yl)-1H-indol-5-yl]-(3,5-dichloro-phenylsulphonyl)-amino]-methyl}-posponic acid | 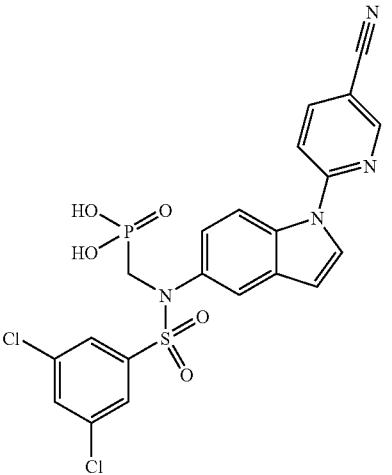 [SMILES: N#Cc1ccc(-n2ccc3cc(N(CP(=O)(O)O)S(=O)(=O)c4cc(Cl)cc(Cl)c4)ccc32)nc1] |
| (61) | [((3,5-dichloro-phenylsulphonyl)-{1-[6-(2-hydroxy-ethoxy)-pyridazin-3-yl]-1H-indol-5-yl}-amino)-methyl]-phosphonic acid | 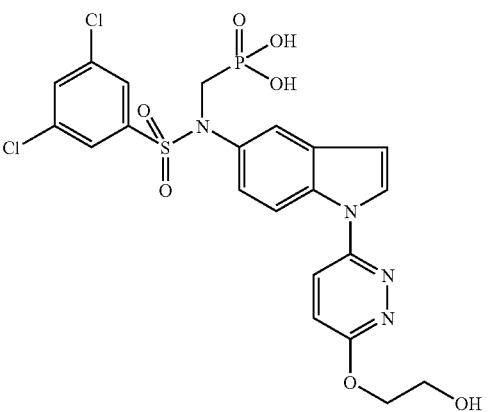 [SMILES: O=P(O)(O)CN(c1ccc2c(ccn2-c2ccc(OCCO)nn2)c1)S(=O)(=O)c1cc(Cl)cc(Cl)c1] |

| No. | Name | Structural formula |
|---|---|---|
| (62) | {[[1-(5-carbamoyl-pyrazin-2-yl)-1H-indol-5-yl]-(3,5-dichloro-phenylsulphonyl)-amino]-methyl}-phosphonic acid | 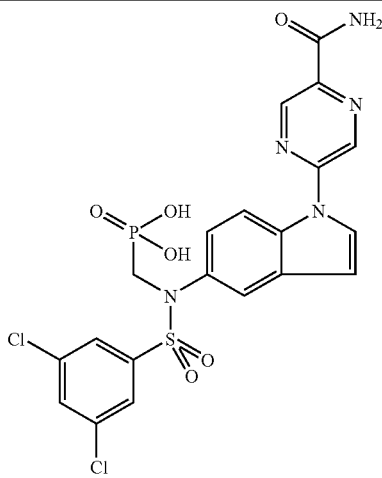 |
| (63) | ({(3,5-dichloro-phenylsulphonyl)-[1-(5-methanesulphonyl-pyrazin-2-yl)-1H-indol-5-yl]-amino}-methyl)-phosphonic acid | 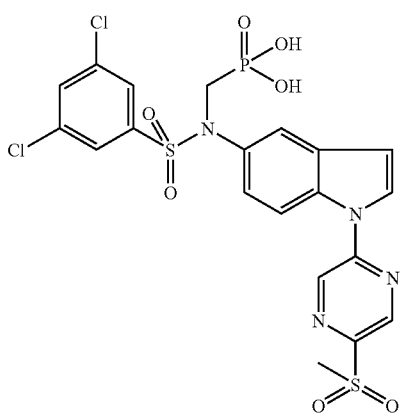 [SMILES: CS(=O)(=O)c1cnc(-n2ccc3cc(N(CP(=O)(O)O)S(=O)(=O)c4cc(Cl)cc(Cl)c4)ccc32)cn1] |

Example 2

Coated Tablets Containing 75 mg of Active Substance 1 tablet core contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg
die: 9 mm, convex

The tablet cores thus produced are coated with a film consisting essentially of hydroxypropylmethylcellulose. The finished film-coated tablets are polished with beeswax.

Weight of coated tablet: 245 mg.

Example 3

Tablets Containing 100 mg of Active Substance

Composition:

1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.
Weight of tablet: 220 mg
Diameter: 10 mm, biplanar, facetted on both sides and notched on one side.

Example 4

Tablets Containing 150 mg of Active Substance

Composition:
1 tablet contains:

| | |
|---|---|
| active substance | 50.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:
The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.
Weight of tablet: 300 mg
die: 10 mm, flat

Example 5

Hard Gelatine Capsules Containing 150 mg of Active Substance 1 capsule contains:

| | |
|---|---|
| active substance | 150.0 mg |
| corn starch (dried) | approx. 80.0 mg |
| lactose (powdered) | approx. 87.0 mg |
| magnesium stearate | 3.0 mg |
| | approx. 420.0 mg |

Preparation:
The active substance is mixed with the excipients, passed through a screen with a mesh size of 0.75 mm and homogeneously mixed using a suitable apparatus. The finished mixture is packed into size 1 hard gelatine capsules.
Capsule filling: approx. 320 mg
Capsule shell: size 1 hard gelatine capsule.

Example 6

Suppositories Containing 150 mg of Active Substance 1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:
After the suppository mass has been melted the active substance is homogeneously distributed therein and the melt is poured into chilled moulds.

Example 7

Suspension Containing 50 mg of Active Substance 100 ml of suspension contain:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:
The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.
5 ml of suspension contain 50 mg of active substance.

Example 8

Ampoules Containing 10 mg Active Substance

Composition:

| | |
|---|---|
| active substance | 10.0 mg |
| 0.01 N hydrochloric acid | q.s. |
| double-distilled water | ad 2.0 ml |

Preparation:
The active substance is dissolved in the necessary amount of 0.01 N HCl, made isotonic with common salt, filtered sterile and transferred into 2 ml ampoules.

Example 9

Ampoules Containing 50 mg of Active Substance

Composition:

| | |
|---|---|
| active substance | 50.0 mg |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

The invention claimed is:

1. A compound of formula

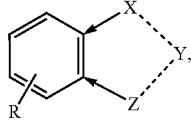
(I)

wherein
R denotes a group of formula

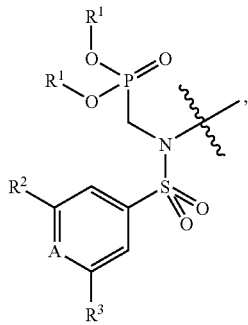

wherein
$R^1$ denotes H, $C_{1-6}$-alkyl-carbonyl-oxy-$C_{1-3}$-alkyl or $C_{1-6}$-alkoxy-carbonyl-oxy-$C_{1-3}$-alkyl,
$R^2$ and $R^3$ independently of one another denote H, halogen, $C_{1-3}$-alkyl, $C_{1-3}$-perfluoroalkyl, $C_{1-3}$-perfluoroalkoxy, $C_{1-3}$-alkoxy, cyano or nitro
and
A denotes CH or N,
and the heterocyclic group

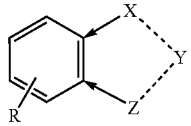

denotes a group of formula

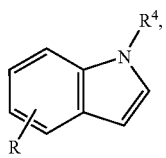
(Ia)

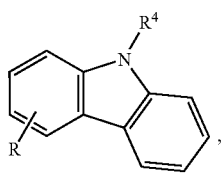
(Ib)

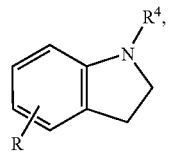
(Ic)

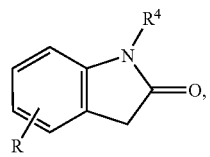
(Id)

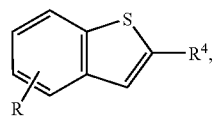
(Ie)

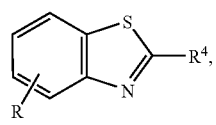
(If)

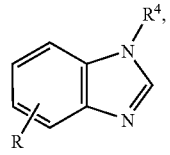
(Ig)

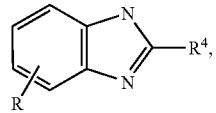
(Ih)

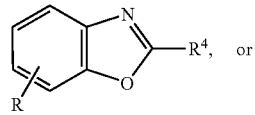
(Ii) or

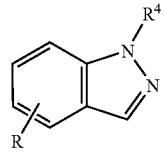
(Ij)

wherein the above-mentioned heterocycles of formulae (Ia), (Ic), (Id), (Ie), (Ig) and (Ij) may optionally be substituted at the carbon atoms of the 5 ring in each case by one or two groups selected from among halogen, $C_{1-3}$-alkyl, cyano, $C_{1-3}$-perfluoroalkyl, $C_{3-6}$-cycloalkyl $C_{2-4}$-alkynyl, $C_{2-4}$-alkenyl, $C_{1-3}$-alkyl-carbonyl, $C_{1-3}$-perfluoroalkyl-carbonyl, carboxyl, aminomethyl, $C_{1-3}$-alkyl-aminomethyl, di-($C_{1-3}$-alkyl)-aminomethyl, aminocarbonyl, $C_{1-3}$-alkyl-aminocarbonyl or di-($C_{1-3}$-alkyl)-aminocarbonyl, wherein the groups are identical or different and each carbon atom can only carry one group, and wherein $R^4$ denotes a 1H-pyrimidin-2,4-dionyl or 2H-pyridazin-3-onyl group optionally mono- or disubstituted by one or two methyl groups or an optionally substituted aryl or heteroaryl group, or the tautomers, stereoisomers, mixtures thereof and salts thereof.

2. A compound of formula (I) according to claim 1, wherein

R denotes a group of the formula mentioned in claim 1, wherein $R^1$ denotes H, $C_{1-6}$-alkyl-carbonyl-oxy-$C_{1-2}$-alkyl or $C_{1-6}$-alkoxy-carbonyl-oxy-$C_{1-2}$-alkyl $R^2$ and $R^3$ independently of one another denote halogen, $C_{1-3}$-alkyl, $C_{1-3}$-perfluoroalkyl, $C_{1-2}$-alkoxy or cyano and A denotes CH or N, and the heterocyclic group

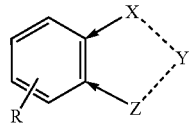

denotes a group of formula

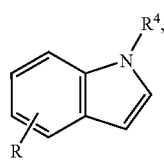
(Ia)

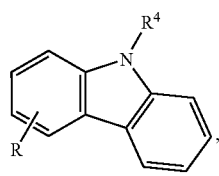
(Ib)

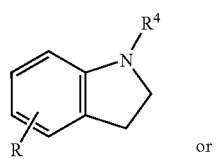
(Ic)

or

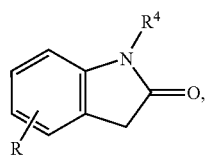
(Id)

wherein the above-mentioned heterocycles of formulae (Ia), (Ic) and (Id) may optionally be substituted at the carbon atoms of the 5 ring by one or two groups selected from among halogen, $C_{1-3}$-alkyl, cyano, $C_{1-3}$-perfluoroalkyl, $C_{3-6}$-cycloalkyl, $C_{1-3}$-alkyl-carbonyl, $C_{1-3}$-perfluoroalkyl-carbonyl, aminocarbonyl, $C_{1-3}$-alkyl-aminocarbonyl or di-($C_{1-3}$-alkyl)-aminocarbonyl, while the groups are identical or different and each carbon atom carries at most one group, and wherein $R^4$ denotes a 1H-pyrimidin-2,4-dionyl or 2H-pyridazin-3-onyl group optionally mono- or disubstituted by one or two methyl groups or an optionally substituted aryl or heteroaryl group while by an optionally substituted aryl or heteroaryl group is meant a phenyl or naphthyl group, wherein one to three methyne groups may be replaced in each case by a nitrogen atom, or a thiazolyl, thiadiazolyl, pyrazolyl or imidazolyl group, which may be mono-, di- or trisubstituted in each case by halogen, cyano, trifluoromethyl or hydroxy, $C_{1-4}$-alkyloxy, which may optionally be substituted from position 2 by a hydroxy, amino, $C_{1-4}$-alkyl-amino or di-($C_{1-3}$-alkyl)-amino group, $C_{3-7}$-cycloalkyl, $C_{3-7}$-cycloalkyloxy or $C_{3-7}$-cycloalkylamino, while in the 5- to 7-membered cycloalkyl moieties in each case a methylene group may be replaced by an oxygen atom, $C_{1-4}$-alkyl, which may be substituted by an amino or hydroxy group, amino, $C_{1-4}$-alkyl-amino, di-($C_{1-3}$-alkyl)-amino, $C_{1-3}$-alkyl-carbonylamino or $C_{3-7}$-cycloalkyl-amino, while the $C_{1-4}$-alkyl-amino- and di-($C_{1-3}$-alkyl)-amino groups in the alkyl moiety may be substituted in each case from position 2 by a hydroxy, amino, $C_{1-4}$-alkyl-amino, di-($C_{1-3}$-alkyl)-amino, $C_{1-3}$-alkyl-carbonylamino or $C_{1-3}$-alkyl-sulphonylamino group, aminocarbonyl, ($C_{1-3}$-alkyl-amino)-carbonyl, [di-($C_{1-3}$-alkyl)-amino]-carbonyl, $C_{3-7}$-cycloalkyl-aminocarbonyl, $C_{1-3}$-alkyl-carbonyl or $C_{1-4}$-alkoxy-carbonyl, $C_{1-3}$-alkylsulphonyl, $C_{1-3}$-alkylsulphinyl or $C_{1-3}$-alkyl-sulphanyl, oxazolyl, thiazolyl, oxoimidazolidinyl or imidazolyl, which may optionally be substituted by a $C_{1-3}$-alkyl group, or a 5- to 7-membered cycloalkyleneimio group wherein a methyne group may be replaced by an oxygen or sulphur atom or by an —NH, —N($C_{1-3}$-alkylsulphonyl) or —N($C_{1-3}$-alkyl-carbonyl)-group and optionally a further methyne group may be replaced by a carbonyl, sulphinyl or sulphonyl group, while the substituents may be identical or different, or the tautomers, stereoisomers, mixtures thereof and salts thereof.

3. A compound of formula (I) according to claim 1, wherein

R denotes a group of the formula mentioned in claim 1, wherein $R^1$ denotes H, $C_{1-4}$-alkyl-carbonyl-oxy-$C_{1-2}$-alkyl or $C_{1-4}$-alkoxy-carbonyl-oxy-$C_{1-2}$-alkyl, $R^2$ and $R^3$ independently of one another represent chlorine, bromine or $C_{1-2}$-alkyl and A denotes CH or N, and the heterocyclic group

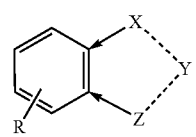

denotes a group of formula

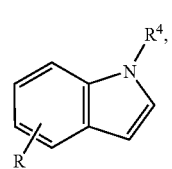
(Ia)

-continued

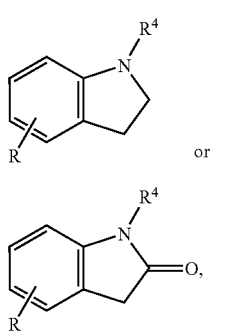

while the heterocyclic groups mentioned above may optionally be substituted at the carbon atoms of the 5 ring by a group selected from among chlorine, $C_{1-2}$-alkyl, cyano and trifluoromethyl, and wherein $R^4$ denotes a 1H-pyrimidin-2,4-dionyl or 2H-pyridazin-3-onyl group optionally mono- or disubstituted by one or two methyl groups or an optionally substituted aryl or heteroaryl group, while by an optionally substituted aryl or heteroaryl group is meant a phenyl, pyridinyl, pyrimidinyl, pyrazinyl, pyridazinyl, triazinyl, thiazolyl, thiadiazolyl, pyrazolyl or imidazolyl group, which may be mono- or disubstituted in each case by chlorine, bromine, cyano or trifluoromethyl, $C_{1-4}$-alkyloxy, which optionally may be substituted from position 2 by a hydroxy, amino, $C_{1-4}$-alkyl-amino or di-($C_{1-3}$-alkyl)-amino group, $C_{5-7}$-cycloalkyloxy or $C_{5-7}$-cycloalkylamino, while in the 5- to 7-membered cycloalkyl moieties a methylene group is replaced by an oxygen atom in each case, $C_{1-4}$-alkyl, which may be substituted by an amino or hydroxy group, amino, $C_{1-4}$-alkyl-amino, di-($C_{1-3}$-alkyl)-amino, $C_{1-3}$-alkyl-carbonylamino or $C_{3-5}$-cycloalkyl-amino, while the $C_{1-4}$-alkyl-amino- and di-($C_{1-3}$-alkyl)-amino groups in the alkyl moiety may in each case be substituted from position 2 by a hydroxy, amino, $C_{1-4}$-alkyl-amino, di-($C_{1-3}$-alkyl)-amino, $C_{1-3}$-alkyl-carbonylamino or $C_{1-3}$-alkyl-sulphonylamino group, aminocarbonyl, ($C_{1-3}$-alkyl-amino)-carbonyl, [di-($C_{1-3}$-alkyl)-amino]-carbonyl, $C_{3-5}$-cycloalkyl-aminocarbonyl, $C_{1-3}$-alkyl-carbonyl or $C_{1-4}$-alkoxy-carbonyl, $C_{1-3}$-alkylsulphonyl, $C_{1-3}$-alkylsulphinyl or $C_{1-3}$-alkylsulphanyl, oxazolyl, thiazolyl, oxoimidazolidinyl or imidazolyl, which may optionally be substituted by a $C_{1-3}$-alkyl group, or a 5- to 7-membered cycloalkyleneimio group wherein a methyne group may be replaced by an oxygen or sulphur atom or by an —NH, —N($C_{1-3}$-alkylsulphonyl) or —N($C_{1-3}$-alkylcarbonyl)-group and optionally a further methyne group is replaced by a carbonyl, sulphinyl or sulphonyl group, while the substituents may be identical or different, or the tautomers, stereoisomers, mixtures thereof and salts thereof.

4. A compound of formula (I) according to claim 1, wherein

R denotes a group of the formula mentioned in claim 1, wherein $R^1$ denotes H, tert.-butylcarbonyloxymethyl or iso-propyloxycarbonyloxymethyl, $R^2$ and $R^3$ independently of one another represent chlorine, bromine or methyl and A denotes CH, and the heterocyclic group

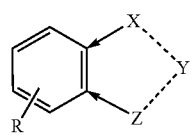

denotes a group of formula

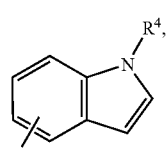

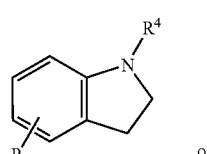

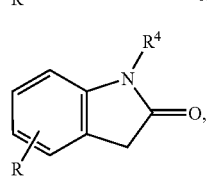

while the heterocyclic groups mentioned above may optionally be substituted at the carbon atom of the 5 ring adjacent to the phenyl ring by a methyl group or ethyl group and $R^4$ denotes an optionally substituted aryl or heteroaryl group, while by an optionally substituted aryl or heteroaryl group is meant a phenyl, pyridinyl, pyrimidinyl, pyrazinyl, pyridazinyl or imidazolyl group, which may be substituted in each case by one or two substituents selected from chlorine, methyl, ethyl, iso-propyl, amino, methylamino, dimethylamino, aminocarbonyl, methylaminocarbonyl, dimethylaminocarbonyl, methylsulphonyl, methylsulphinyl, methylsulphanyl, 2-oxo-imidazolidinyl, morphonin-4-yl, piperazin-1-yl and 4-methyl-piperazin-1-yl, while the substituents may be identical or different, or the tautomers, stereoisomers, mixtures thereof and salts thereof.

5. A compound of formula (I) according to claim 1, wherein
R denotes a group of the formula mentioned in claim 1, wherein
$R^1$ denotes hydrogen,
$R^2$ and $R^3$ in each case represent chlorine and
A denotes the group >CH,
and the heterocyclic group

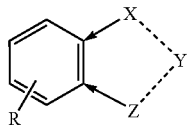

denotes a group of formula

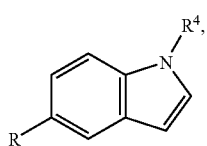 (Ia1)

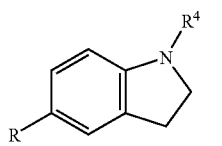 (Ic1)

or

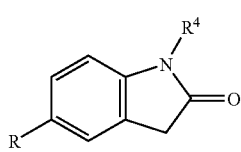 (Id1)

wherein
$R^4$ denotes a phenyl, pyrimidinyl, pyridazinyl or imidazolyl group, which may be substituted in each case by one or two chlorine atoms or a methyl or 2-oxo-imidazolidinyl group,
or the tautomers, stereoisomers, mixtures thereof and salts thereof.

6. A compound according to claim 1 selected from:
(1) {[(3,5-dichloro-phenylsulphonyl)-(1-pyrimidin-2-yl-2,3-dihydro-1H-indol-5-yl)-amino]-methyl}-phosphonic acid,
(2) {[[1-(2-chloro-phenyl)-2-oxo-2,3-dihydro-1H-indol-5-yl]-(3,5-dichloro-phenylsulphonyl)-amino]-methyl}-phosphonic acid,
(3) ({(3,5-dichloro-phenylsulphonyl)-[1-(2,6-dichloro-phenyl)-2-oxo-2,3-dihydro-1H-indol-5-yl]-amino}-methyl)-phosphonic acid,
(4) ({(3,5-dichloro-phenylsulphonyl)-[1-(1-methyl-1H-imidazol-2-yl)-2,3-dihydro-1H-indol-5-yl]-amino}-methyl)-phosphonic acid,
(5) ({(3,5-dichloro-phenylsulphonyl)-[1-(6-methyl-pyridazin-3-yl)-1H-indol-5-yl]-amino}-methyl)-phosphonic acid and
(6) [((3,5-dichloro-phenylsulphonyl)-{1-[6-(2-oxo-imidazolidin-1-yl)-pyridazin-3-yl]-1H-indol-5-yl}-amino)-methyl]-phosphonic acid,
or the enantiomers thereof, the mixtures thereof and the salts thereof.

7. A physiologically acceptable salt of the compound according to claim 1 with an inorganic or organic acid or base.

8. Method of using a compound according to claim 1 for the treatment of type I and type II diabetes mellitus.

9. A pharmaceutical composition containing a compound according to claim 1 or a salt thereof, optionally together with one or more inert carriers and/or diluents.

10. Process for preparing a pharmaceutical composition comprising incorporating a compound of claim 1, or a salt thereof, in one or more inert carriers and/or diluents by a non-chemical method.

11. Process for preparing the compound of formula I according to claim 1, characterised in that
a compound of general formula (IV)

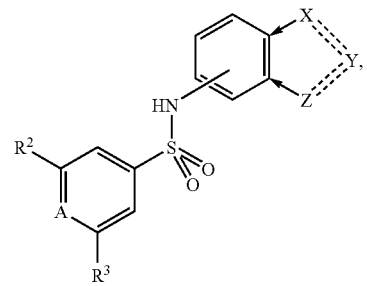 (IV)

wherein $R^2$, $R^3$, X, Y, Z and A are defined as in claim 1, is alkylated by means of a compound of general formula $(R^1-O-)_2P(=O)-CH_2-X$, wherein X denotes a leaving group,
and
if desired any protective group used to protect reactive groups during the reactions is cleaved afterwards or simultaneously and/or
a compound of general formula I thus obtained is resolved into its stereoisomers and/or
a compound of general formula I thus obtained is converted into the salts thereof,
particularly for pharmaceutical use into the physiologically acceptable salts thereof with an inorganic or organic acid or base.

* * * * *